US008207337B2

(12) United States Patent
Miyaura et al.

(10) Patent No.: US 8,207,337 B2
(45) Date of Patent: Jun. 26, 2012

(54) REAGENT FOR ORGANIC SYNTHESIS REACTION CONTAINING ORGANIC TRIOL BORATE SALT

(75) Inventors: Norio Miyaura, Sapporo (JP); Yasunori Yamamoto, Sapporo (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 444 days.

(21) Appl. No.: 12/524,821

(22) PCT Filed: Jan. 28, 2008

(86) PCT No.: PCT/JP2008/051208
§ 371 (c)(1),
(2), (4) Date: Jul. 28, 2009

(87) PCT Pub. No.: WO2008/093637
PCT Pub. Date: Aug. 7, 2008

(65) Prior Publication Data
US 2010/0087646 A1 Apr. 8, 2010

(30) Foreign Application Priority Data

Jan. 29, 2007 (JP) ................................. 2007-017286
Jan. 21, 2008 (JP) ................................. 2008-010543

(51) Int. Cl.
*C07F 5/02* (2006.01)
*C07D 333/04* (2006.01)

(52) U.S. Cl. ................... 546/13; 549/4; 549/213; 568/1; 568/3

(58) Field of Classification Search .................... 546/13; 549/4, 213; 568/1, 3
See application file for complete search history.

(56) References Cited

U.S. PATENT DOCUMENTS 2,909,560 A 10/1959 McManimie
4,985,305 A 1/1991 Schubart et al.

FOREIGN PATENT DOCUMENTS

| CA | 2 285 578 A1 | 7/2001 |
| JP | 1-257043 A | 10/1989 |
| JP | 11-116580 A | 4/1999 |
| JP | 2000-212195 A | 8/2000 |
| WO | WO 2005/105817 A2 | 11/2005 |

OTHER PUBLICATIONS

International Search Report of PCT/JP2008/051208, dated Mar. 18, 2008.
Cammidge et al. "Aryl Trihydroxyborates : Easily Isolated Discrete Species Convenient for Direct Application in Coupling Reactions." Organic Letters, vol. 8(18), 2006, pp. 4071-4074.
Yasuda. "Cage-Shaped Borate Esters with Enhanced Lewis Acidity and Catalytic Activity." Organic Letters, vol. 8(4), 2006, pp. 761-764.
Rose et al. "Negative-ion Electrospray and Fast Atom Bombardment Mass Spectrometery of Esters of Boron Acids." Organic Mass Spectrometry, vol. 27(8), 1992, pp. 876-882.
Matteson et al. "Hydrolysis of Substituted 1,3,2-Dioxaborolanes and an Asymmetric Synthesis of a Differentially Protected *syn,sun*-3-Methyl-2, 4-hexanediol." Journal of Organic Chemistry, vol. 61(17), 1996, pp. 6047-6051.

*Primary Examiner* — Charanjit Aulakh
(74) *Attorney, Agent, or Firm* — Hamre, Schumann, Mueller & Larson, P.C.

(57) ABSTRACT

[Problem]
To provide an organoboron compound-containing reagent for organic synthesis reactions which undergoes no trimerization with dehydration, does not necessitate activation with a base, and is stable and highly active.

[Means for Solving Problems]
The reagent for organic synthesis reactions contains an organic triol borate salt represented by any of the general formulae (I) to (III) and general formula (XVI): (wherein $R^1$ represents alkyl, alkenyl, etc.; $R^2$ represents optionally substituted alkyl, alkenyl, alkynyl, etc. or represents hydrogen; $m^+$ represents an alkaline metal ion, phosphonium ion, or given ammonium ion; $M^{2+}$ represents an alkaline earth metal; X represents halogen or alkoxide; Y represents an alkali metal ion, etc.; A represents optionally substituted methylene; and n represents an integer).

13 Claims, No Drawings

REAGENT FOR ORGANIC SYNTHESIS REACTION CONTAINING ORGANIC TRIOL BORATE SALT

TECHNICAL FIELD

The present invention relates to a reagent for organic synthesis reaction containing the suitable organic triol borate salt when using as a reaction reagent for organic synthesis reaction, the cross coupling reaction method and the addition reaction method, using the said reagent, and the use as a reagent for organic synthesis reaction, the organic triol borate salt.

BACKGROUND ART

Organic boron compounds are frequently used for organic synthesis due to its easy handling, and at present, more than 300 kinds of organic boron compounds are distributing in the market. In addition, various novel organic boron compounds are being developed.

However, it is difficult to obtain the pure boronic acids because they undergo easily dehydration and trimerization due to forming cyclic anhydride. Therefore, there are any problems that stoichiometric ratio of reactants when used for the reaction is not be determined, and a large amount of boronic acid must be used compared with theoretical amounts, and reagent cost becomes a problem in the case of the expensive reagent. In addition, the well known boronic acids are generally less reactive, therefore, there is a problem of the necessity of activating them by base etc.

Then, in recent years, organic boronic acid esters and organic trifluoroborate potassium salts, which do not undergo trimerization with dehydration, have been developed (Patent Document 3, Non-Patent Document 2). However, these organic boron compounds, also, are less reactive, thus, have such a problem as the necessity of activation treatment, for example, by adding a base etc. in reaction.

In addition, trihydroxy borate salt or trialkoxy borate salt has been investigated (Patent Document 4, Non-Patent Document 1). However, since these have the structure that three hydroxyl groups or alkoxy groups locate independently, these compounds are easily dissociated and less stable, therefore isolation thereof becomes difficult.

Although the other various novel organic boron compounds are being investigated, these compounds are not investigated whether they are able to use as the organic boron reagents or not. (Patent Document 1, Patent Document 2, Patent Document 5).

Moreover, the organic triol borate salts having different structure are disclosed (Non-Patent Document 4).

Further, generally, in the case of cross coupling reaction of organic boronic acid to be carried out in basic aqueous solution, hydrolysis of C—B bonding may be carried out competitively, therefore, a large excess of boronic acid may be required. Such a circumstance is remarkable in hetero aromatic boronic acid, in particular, 2-pyridine boronic acid hydrolyzes very quickly, therefore, due to poor practicality, there are no examples used in reaction.

Under such a circumstance, developments of novel organic boron compounds undergoing no trimerization with dehydration, having high reactivity and excellent storage stability are expected.

[Patent Document 1] JP-A-11-116580
[Patent Document 2] JP-A-2000-212195
[Patent Document 3] CA-A1-2285578
[Patent Document 4] WO 2005/105817
[Patent Document 5] U.S. Pat. No. 2,909,560
[Non patent Document 1] Organic Letters 2006, 8, 4071
[Non patent Document 2] Organic Letters 2006, 8, 761
[Non patent Document 3] Organic Mass spectrometry 1992, 27, 876
[Non patent Document 4] J. Org. Chem., Vol 0.61, No. 17, 1996

DISCLOSURE OF INVENTION

Problem to be Solved by the Invention

It is an object of the present invention to provide the reagent for organic synthesis reaction containing the stable and high reactive organic boron compound undergoing no formation of trimerization with dehydration and no necessity of activation by base.

Means for Solving the Problem

The present invention is:

(1) The reagent for organic synthesis reaction including at least one among the organic triol borate salts represented by the following general formulae (I) to (III) and (XVI):

[Formula 1]

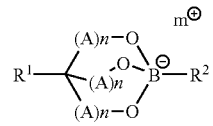

(I)

[Formula 2]

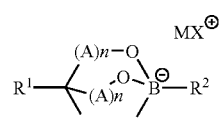

(II)

[Formula 3]

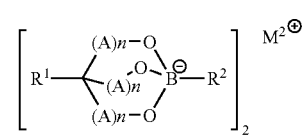

(III)

[Formula 18]

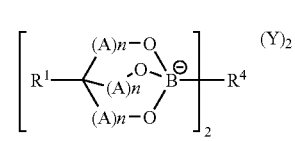

(XVI)

(wherein $R^1$ represents alkyl group, alkenyl group, alkynyl group, aryl group or aralkyl group; $R^2$ represents alkyl group, alkenyl group, alkynyl group, aryl group, aralkyl group or heterocyclic group, which may have a substituent group, or hydrogen atom; $R^4$ represents divalent aromatic hydrocarbon group or heterocyclic group, which may have a substituent group; m⁺ represents alkaline metal ion, phosphonium ion, or ammonium ion represented by general formula (IV):

[Formula 4]

(IV)

(wherein R³ represents alkyl group); M²⁺ represents an alkaline earth metal ion, X represents halogen or alkoxide; Y represents alkaline metal ion, phosphonium ion, ammonium ion represented by general formula (IV), or the group represented by general formula (XVII):

[Formula 19]

(XVII)

(wherein M represents an alkaline earth metal, X represents halogen atom or alkoxide); A represents a methylene group which may have a substituent group; n represents an integer of 1 or more which may be the same or the different, respectively.
(2) The present invention is the cross coupling method, which comprises reacting the reagent for organic synthesis reaction described in the above-described (1) with organic halide, amine, alcohol or thioalcohol compound in the presence of palladium catalyst, nickel catalyst or copper catalyst.
(3) The present invention is the addition reaction method, which comprises reacting the reagent for organic synthesis reaction described in the above-described (1) with the electron-withdrawing group substituted olefin compound, carbonyl compound or imine compound in the presence of rhodium catalyst or palladium catalyst.
(4) The present invention is the use as the reagent for organic synthesis reaction by at least one among the organic triol borate salts represented by the above-described general formulae (I) to (III) and (XVI); and
(5) The present invention is the organic triol borate salt represented by at least one among the above-described general formulae (I) to (III) and (XVI).

Namely, the present inventors have intensively studied a way to solve the above-described problems, and as a result, have found that by using the organic triol borate salt having specific structure, for example, organic synthesis reaction such as carbon-carbon bond formation reaction, carbon-nitrogen bond formation reaction, carbon-oxygen bond formation reaction, carbon-sulfur bond formation reaction, specifically, for example, cross coupling reaction or addition reaction can be effectively carried out, and have thus completed the present invention.

Effects of the Invention

The organic triol borate salts according to the present invention can be obtained as a pure compound because of undergoing no trimerization with dehydration, and also as a stable and high reactive compound because of necessitating no activation with base. Further, the relevant organic trial borate salt can react in anhydrous organic solvent, therefore, when this is used as, for example, the reagent for organic synthesis reaction (particularly, cross coupling reaction, addition reaction, etc.) such as carbon-carbon bond formation reaction, carbon-nitrogen bond formation reaction, carbon-oxygen bond formation reaction or carbon-sulfur bond formation reaction, the reaction can be effectively carried out. Especially, conventional boron reagents were not able to use substantially as boron reagent for organic synthesis reaction such as the reagent for coupling reaction such as, for example, pyridylation because C—B bonding was easily cleaved by hydrolysis. When the organic trial borate salts of the present invention corresponding to, for example, heterocyclic boronic acid such as 2-pyridine boronic acid, 2-thiophene boronic acid, 2-pyrrole boronic acid and 2-furan boronic acid; or 2-alkynyl boronic acid are used, the cross coupling reaction such as pyridylaction can be efficiently carried out.

BEST MODE FOR CARRYING OUT THE INVENTION

The reagent for organic synthesis reaction of the present invention includes at least one among organic trial borate salts represented by the above-described general formulae (I) to (III) and (XVI), and may include two or three kinds among salts represented by the above-described general formulae (I) to (III) and (XVI), further, may contain all of four kinds of salts.

The alkyl group represented by R¹ in general formula (I) to (III) and (XVI) may be any of straight chained, branched or cyclic group, and includes one having generally 1 to 10 carbon atoms, preferably 1 to 6 carbon atoms, more preferably, 1 to 4 carbon atoms, specifically, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, 2-methylbutyl group, 1-ethylpropyl group, n-hexyl group, isohexyl group, sec-hexyl group, tert-hexyl group, neohexyl group, 2-methylpentyl group, 3-methylpentyl group, 1,2-dimethylbutyl group, 2,2-dimethylbutyl group, 1-ethylbutyl group, 2-ethylbutyl group, n-heptyl group, isoheptyl group, sec-heptyl group, tert-heptyl group, neoheptyl group, 2-methylhexyl group, 3-methylhexyl group, 2,2-dimethylpentyl group, 3-ethylpentyl group, 2,4-dimethylpentyl group, 1-ethyl-1-methylbutyl group, 1,2,3-trimethylbutyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group or cyclodecyl group. Among them, methyl group, ethyl group or tert-butyl group is preferable, in particular, methyl group is more preferable.

The alkenyl group represented by R¹ may be any of straight chained, branched or cyclic group, and includes one having generally 2 to 12 carbon atoms, preferably 2 to 6 carbon atoms, specifically, for example, vinyl group, allyl group, 1-propenyl group, isopropenyl group, 1-butenyl group, 2-butenyl group, 3-butenyl group, 2-methylallyl group, 1-pentenyl group, 2-pentenyl group, 3-pentenyl group, 4-pentenyl group, 2-methyl-2-butenyl group, 1-hexenyl group, 2-hexenyl group, 3-hexenyl group, 5-hexenyl group, 2-methyl-2-pentenyl group, 1-heptenyl group, 2-heptenyl group, 3-heptenyl group, 4-heptenyl group, 5-heptenyl group, 6-heptenyl group, 1-octenyl group, 2-octenyl group, 1-nonenyl group, decenyl group, undecenyl group, 1-dodecenyl group, 2-dodecenyl group, 3-dodecenyl group, 4-dodecenyl group, 5-dodecenyl group, 6-dodecenyl group, 7-dodecenyl group, 8-dodecenyl group, 9-dodecenyl group, 10-dodecenyl group, 11-dodecenyl group, 1-cyclobutenyl group, 1-cyclopentenyl group or 1-cyclohexenyl group.

The alkynyl group represented by R¹ may be any of straight chained, branched or cyclic group, and includes one having generally 2 to 12 carbon atoms, preferably 2 to 6 carbon atoms, specifically, for example, ethynyl group, 1-propynyl group, 2-propynyl group, 1-butynyl group, 2-butynyl group, 3-butynyl group, 1-methyl-2-propynyl group, 1-pentynyl group, 2-pentynyl group, 3-pentynyl group, 4-pentynyl group, 1-methyl-3-butynyl group, 1-hexynyl group, 2-hexynyl group, 3-hexynyl group, 4-hexynyl group, 5-hexynyl group, 2-methyl-4-heptynyl group, 1-heptynyl group, 2-heptynyl group, 3-heptynyl group, 4-heptynyl group, 5-heptynyl group, 6-heptynyl group, 1-octynyl group, 2-octynyl group, 3-octynyl group, 4-octynyl group, 5-octynyl group, 6-octynyl group, 7-octynyl group, 1-nonynyl group, 2-nonynyl group, 3-nonynyl group, 4-nonynyl group, 5-nonynyl group, 6-nonynyl group, 7-nonynyl group, 8-nonynyl group, 1-decynyl group, 3-decynyl group, 5-decynyl group, 7-decynyl group, 9-decynyl group, 1-undecynyl group, 3-undecynyl group, 5-undecynyl group, 7-undecynyl group, 9-undecynyl group, 1-dodecynyl group, 3-dodecynyl group, 5-dodecynyl group, 7-dodecynyl group, 9-dodecynyl group or 11-dodecynyl group.

The aryl group represented by $R^1$ includes generally one having 6 to 10 carbon atoms, specifically, for example, phenyl group or naphthyl group. In particular, phenyl group is preferable.

These aryl groups may contain generally 1 to 5 substituent groups, and the said substituent group includes, for example, alkyl group having 1 to 4 carbon atoms such as methyl group, ethyl group, n-propyl group, isopropyl group, n-butyl group, isobutyl group, sec-butyl group and tert-butyl group; for example, aryl group such as phenyl group; for example, halogen atom such as fluorine atom, chlorine atom, bromine atom and iodine atom; for example, alkoxycarbonyl group having 1 to 3 carbon atoms such as methoxycarbonyl group, ethoxycarbonyl group, n-propoxycarbonyl group and isopropoxycarbonyl group; for example, aryloxy group such as phenoxy group.

The aralkyl group represented by $R^1$ includes generally one having 7 to 12, specifically, for example, benzyl group, phenethyl group, phenylpropyl group, phenylbutyl group, phenylpentyl group or phenylhexyl group. In particular, benzyl group is preferable.

The alkyl group of alkyl group which may have a substituent group, represented by R2 may be any of straight chained, branched or cyclic group, and includes generally one having 1 to 20 carbon atoms, preferably 1 to 10 carbon atoms, and includes, specifically, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, 2-methylbutyl group, 1-ethylpropyl group, n-hexyl group, isohexyl group, sec-hexyl group, tert-hexyl group, neohexyl group, 2-methylpentyl group, 3-methylpentyl group, 1,2-dimethylbutyl group, 2,2-dimethylbutyl group, 1-ethylbutyl group, 2-ethylbutyl group, n-heptyl group, isoheptyl group, sec-heptyl group, tert-heptyl group, neoheptyl group, 2-methylhexyl group, 3-methylhexyl group, 2,2-dimethylpentyl group, 3-ethylpentyl group, 2,4-dimethylpentyl group, 1-ethyl-1-methylbutyl group, 1,2,3-trimethylbutyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, n-undecyl group, isoundecyl group, sec-undecyl group, tert-undecyl group, neoundecyl group, n-dodecyl group, isododecyl group, sec-dodecyl group, tert-dodecyl group, neododecyl group, n-tridecyl group, isotridecyl group, sec-tridecyl group, tert-tridecyl group, neotridecyl group, n-tetradecyl group, isotetradecyl group, sec-tetradecyl group, tert-tetradecyl group, neotetradecyl group, n-pentadecyl group, isopentadecyl group, sec-pentadecyl group, tert-pentadecyl group, neopentadecyl group, n-hexadecyl group, isohexadecyl group, sec-hexadecyl group, tert-hexadecyl group, neohexadecyl group, n-heptadecyl group, isoheptadecyl group, sec-heptadecyl group, tert-heptadecyl group, neoheptadecyl group, n-octadecyl group, isooctadecyl group, sec-octadecyl group, tert-octadecyl group, neooctadecyl group, n-nonadecyl group, isononadecyl group, sec-nonadecyl group, tert-nonadecyl group, neononadecyl group, n-icosyl group, isoicosyl group, sec-icosyl group, tert-icosyl group, neoicosyl group, cyclopropyl group, cyclobutyl group, cyclopentyl group, cyclohexyl group, cycloheptyl group, cyclooctyl group, cyclononyl group, cyclodecyl group, cycloundecyl group or cyclododecyl group.

The alkenyl group of alkenyl group which may have a substituent group, represented by $R^2$ in general formula (I) to (III) may be any of straight chained, branched or cyclic group, and includes generally one having 2 to 20 carbon atoms, preferably 1 to 10 carbon atoms, and includes, specifically, for example, vinyl group, allyl group, 1-propenyl group, isopropenyl group, 1-butenyl group, 2-butenyl group, 3-butenyl group, 2-methylallyl group, 1-pentenyl group, 2-pentenyl group, 3-pentenyl group, 4-pentenyl group, 2-methyl-2-butenyl group, 1-hexenyl group, 2-hexenyl group, 3-hexenyl group, 5-hexenyl group, 2-methyl-2-pentenyl group, 1-heptenyl group, 2-heptenyl group, 3-heptenyl group, 4-heptenyl group, 5-heptenyl group, 6-heptenyl group, 1-octenyl group, 2-octenyl group, 1-nonenyl group, decenyl group, undecenyl group, 1-dodecenyl group, 2-dodecenyl group, 3-dodecenyl group, 4-dodecenyl group, 5-dodecenyl group, 6-dodecenyl group, 7-dodecenyl group, 8-dodecenyl group, 9-dodecenyl group, 10-dodecenyl group, 11-dodecenyl group, tridecenyl group, tetradecenyl group, pentadecenyl group, hexadecenyl group, heptadecenyl group, octadecenyl group, nonadecenyl group, icosenyl group, 1-cyclobutenyl group, 1-cyclopentenyl group or 1-cyclohexenyl group.

The alkynyl group of alkynyl group which may have a substituent group, represented by $R^2$ may be any of straight chained, branched or cyclic group, and includes one having 2 to 20 carbon atoms, preferably 2 to 10 carbon atoms, and includes, specifically, for example, ethynyl group, 1-propynyl group, 2-propynyl group, 1-butynyl group, 2-butynyl group, 3-butynyl group, 1-methyl-2-propynyl group, 1-pentynyl group, 2-pentynyl group, 3-pentynyl group, 4-pentynyl group, 1-methyl-3-butynyl group, 1-hexynyl group, 2-hexynyl group, 3-hexynyl group, 4-hexynyl group, 5-hexynyl group, 2-methyl-4-heptynyl group, 1-heptynyl group, 2-heptynyl group, 3-heptynyl group, 4-heptynyl group, 5-heptynyl group, 6-heptynyl group, 1-octynyl group, 2-octynyl group, 3-octynyl group, 4-octynyl group, 5-octynyl group, 6-octynyl group, 7-octynyl group, 1-nonynyl group, 2-nonynyl group, 3-nonynyl group, 4-nonynyl group, 5-nonynyl group, 6-nonynyl group, 7-nonynyl group, 8-nonynyl group, 1-decynyl group, 3-decynyl group, 5-decynyl group, 7-decynyl group, 9-decynyl group, 1-undecynyl group, 3-undecynyl group, 5-undecynyl group, 7-undecynyl group, 9-undecynyl group, 1-dodecynyl group, 3-dodecynyl group, 5-dodecynyl group, 7-dodecynyl group, 9-dodecynyl group, 11-dodecynyl group, tridecynyl group, tetradecynyl group, pentadecynyl group, hexadecynyl group, heptadecanyl group, octadecynyl group, nonadecenyl group or icosynyl group.

The aryl group of aryl group which may have a substituent group, represented by $R^2$ includes generally one having 6 to 10 carbon atoms, specifically, for example, phenyl group or naphthyl group.

The aralkyl group of aralkyl group which may have a substituent group, represented by R² includes generally one having 7 to 20 carbon atoms, specifically, for example, benzyl group, phenethyl group, phenylpropyl group, phenylbutyl group, phenylpentyl group, phenylhexyl group, phenylheptyl group, phenyloctyl group, phenylnonyl group, phenyldecyl group, phenylundecyl group, phenyldodecyl group, phenyltridecyl group or phenyltetradecyl group.

The heterocyclic group of heterocyclic group which may have a substituent group, represented by R² includes, for example, 5-membered ring or 6-membered ring, and includes one having 1 to 3 hetero atoms such as, for example, nitrogen atom, oxygen atom or sulfur atom as hetero atoms, and specifically, includes, for example, thiophenyl group, pyridyl group, indenyl group, furyl group, pyranyl group, imidazolyl group, pyrazolyl group, pyrazinyl group, pyrimidinyl group, pyridazinyl group, pyrrolidinyl group, pyrrolinyl group, imidazolinyl group, pyrazolidinyl group, pyrazolinyl group, piperazinyl group, morpholinyl group, quinuclidinyl group, pyrrolidyl-2-one group, piperidyl group, piperidino group, piperazinyl group, morpholino group, quinuclidinyl group, thiazolyl group, pyrrolyl group, indolyl group, imidazolyl group, purinyl group, quinolyl group, pyranyl group, pyrazyl group, pyrimidyl group, oxazolyl group, 3,4-methylenedioxyphenyl group, 2-benzo[b]thienyl group or the below-represented group.

[Formula 5]

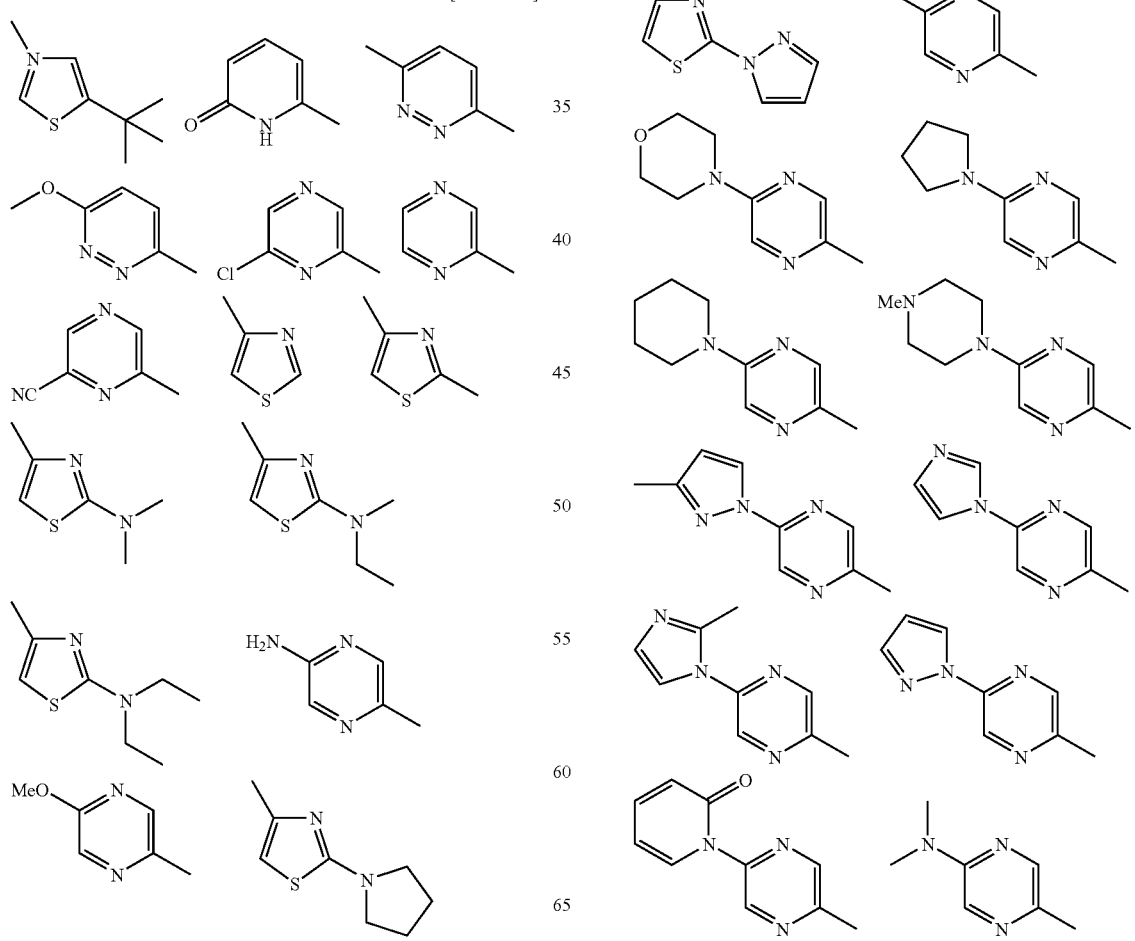

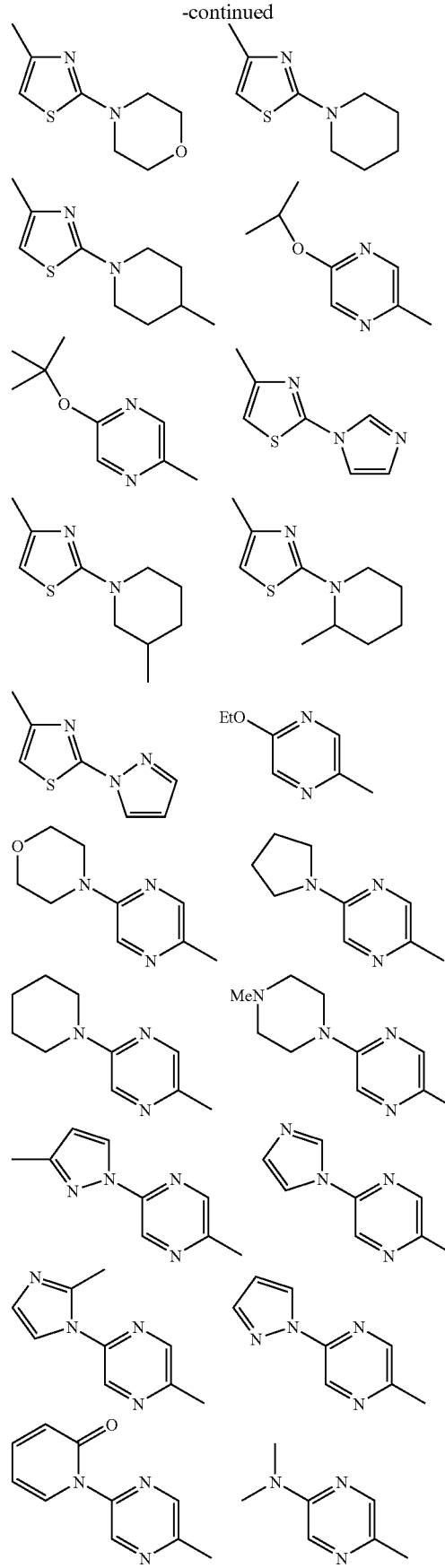

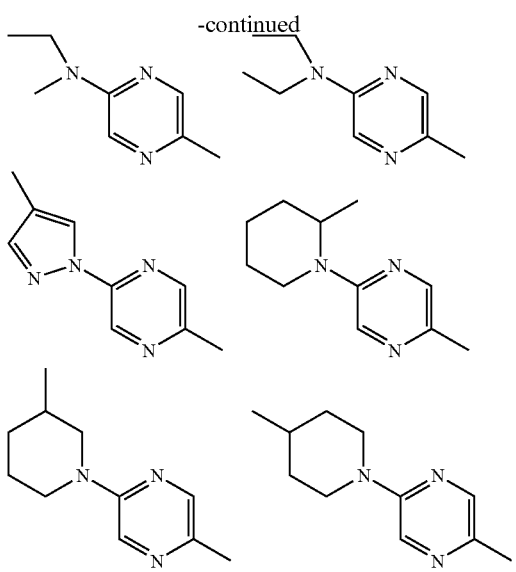

The substituent group of the alkyl group, alkenyl group, alkynyl group, aryl group, aralkyl group and heterocyclic group, which may have a substituent group, represented by $R^2$ includes, for example, alkyl group, alkoxy group, aryl group, aryloxy group, halogen atom or acyl group.

The alkyl group exemplified as substituent group may be any of straight chained, branched or cyclic group, and includes generally one having 1 to 6 carbon atoms, preferably, 1 to 4 carbon atoms, and includes, specifically, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group or neohexyl group.

The alkoxy group exemplified as substituent group may be any of straight chained, branched or cyclic group, and includes generally one having 1 to 6 carbon atoms, preferably, 1 to 4 carbon atoms, and includes, specifically, for example, methoxy group, ethoxy group, n-propoxy group, isopropoxy group, n-butoxy group, isobutoxy group, sec-butoxy group, tert-butoxy group, n-pentyloxy group, isopentyloxy group, sec-pentyloxy group, tert-pentyloxy group, neopentyloxy group, n-hexyloxy group, isohexyloxy group, sec-hexyloxy group, tert-hexyloxy group or neohexyloxy group.

The aryl group exemplified as substituent group includes, for example, phenyl group. The aryloxy group exemplified as substituent group includes, for example, phenoxy group.

The halogen atom exemplified as substituent group includes, for example, fluorine atom, chlorine atom, bromine atom or iodine atom.

The acyl group exemplified as substituent group includes generally one having 2 to 4 carbon atoms, and includes, specifically, for example, acetyl group, propionyl group, butyryl group or isobutyryl group.

Specific example of aryl group having substituent group includes, for example, tolyl group, xylyl group, mesityl group, tert-butylphenyl group, methoxyphenyl group, biphenyl group, pentafluorophenyl group, methoxycarbonylphenyl group (in particular, p-methoxycarbonylphenyl group) or phenoxyphenyl group.

These aralkyl groups may contain generally 1 to 5, preferably, 1 to 3 substituent groups such as, for example, alkoxy group The alkoxy group exemplified as substituent group may be any of straight chained, branched or cyclic group, and includes generally one having 1 to 4 carbon atoms, and specifically, includes, for example, methoxy group, ethoxy group, n-propoxy group, isopropoxy group, n-butoxy group, isobutoxy group, sec-butoxy group, tert-butoxy group, cyclopropoxy group or cyclobutoxy group.

Specific example of aralkyl group having substituent group includes, for example or anisyl group (in particular, m-anisyl group).

The divalent aromatic hydrocarbon group of divalent aromatic hydrocarbon group which may have a substituent group, represented by $R^4$ in general formula (XVI) includes, for example, arylene group or the group represented by general formula (XVIII):

[Formula 20]

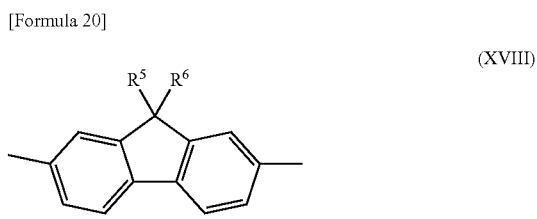

(XVIII)

(wherein $R^5$ and $R^6$ represent each independently alkyl group).

The said arylene group includes generally one having 6 to carbon atoms, and includes, specifically, for example, o-phenylene group, m-phenylene group, p-phenylene group, 1,5-naphthylene group, 1,8-naphthylene group, 2,7-naphthylene group or 2,6-naphthylene group.

The alkyl group represented by $R^5$ to $R^6$ in general formula (XVIII) may be any of straight chained, branched or cyclic group, among them, straight chained or branched one is preferable, and it includes generally one having 1 to 15 carbon atoms, preferably, 1 to 12 carbon atoms, specifically, includes, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, 2-methylbutyl group, 1-ethylpropyl group, n-hexyl group, isohexyl group, sec-hexyl group, tert-hexyl group, neohexyl group, 2-methylpentyl group, 3-methylpentyl group, 1,2-dimethylbutyl group, 2,2-dimethylbutyl group, 1-ethylbutyl group, 2-ethylbutyl group, n-heptyl group, isoheptyl group, sec-heptyl group, tert-heptyl group, neoheptyl group, 2-methylhexyl group, 3-methylhexyl group, 2,2-dimethylpentyl group, 3-ethylpentyl group, 2,4-dimethylpentyl group, 1-ethyl-1-methylbutyl group, 1,2,3-trimethylbutyl group, n-octyl group, isooctyl group, sec-octyl group, tert-octyl group, neooctyl group, 2-ethylhexyl group, n-nonyl group, isononyl group, sec-nonyl group, tert-nonyl group, neononyl group, n-decyl group, isodecyl group, sec-decyl group, tert-decyl group, neodecyl group, n-undecyl group, isoundecyl group, sec-undecyl group, tert-undecyl group, neoundecyl group, n-dodecyl group, isododecyl group, sec-dodecyl group, tert-dodecyl group, neododecyl group, n-tridecyl group, isotridecyl group, sec-tridecyl group, tert-tridecyl group, neotridecyl group, n-tetradecyl group, isotetradecyl group, sec-tetradecyl group, tert-tetradecyl group, neotetradecyl group, n-pentadecyl group, isopentadecyl group, sec-pentadecyl group, tert-pentadecyl group, neopentadecyl group, cyclopropyl group, cyclobutyl group, cyclopentyl group, cyclohexyl group, cycloheptyl group, cyclooctyl group, cyclononyl group or cyclodecyl group.

The hetero ring in the divalent heterocyclic group which may have a substituent group, represented by $R^4$ in general formula (XVI) includes, for example, 5-membered or 6-membered ring having generally one or more, preferably, 1 to 3, more preferably, 1 to 2 hetero atoms such as nitrogen atom, sulfur atom and oxygen atom, and may be monocyclic or polycyclic group, and specifically, includes, for example, 5-membered monocyclic group such as thiophene ring, furan ring, 2H-pyrrole ring, pyrrole ring, imidazole ring, pyrazole ring, thiazole ring, isothiazole ring, isoxazole ring and furazan ring; for example, 6-membered monocyclic group such as pyrane ring, pyridine ring, pyrazine ring, pyrimidine ring and pyridazine ring; for example, condensed bicyclic group consisting of 5-membered and 6-membered ring group such as benzofuran ring, isobenzofuran ring, indolizine ring, isoindole ring, 3H-indole ring, indole ring, 1H-indazole ring, purine ring and benzothiophene ring; for example, condensed bicyclic group consisting of two 6-membered ring groups such as chromene ring, 4H-quinolizine ring, isoquinoline ring, quinoline ring, phthalazine ring, naphthyridine ring, quinoxaline ring and quinazoline ring.

The substituent group of the divalent aromatic hydrocarbon group or the divalent hetero cyclic group, which may have a substituent group, represented by $R^4$ includes, for example, 2,5-bis(hexyloxy)-1,4-phenylene group, 2,3-bis[(trimethylsilyl)ethynyl]-1,4-phenylene group, 2,5-dihexyl-1,4-phenylene group, 2-phenyl-9,10-anthracenyl group, 2-(2-ethylhexyloxy)-5-methoxy-1,4-phenylene group, 2-decyloxy-1,4-phenylene group, 2,5-(phenylethynyl)-1,4-phenylene group, 3,4-bis[2-(trimethylsilyl)ethynyl]-2,5-thiophenenyl group, 3-chloro-2,5-thiophenyl group or 3-hexyl-2,5-thiophenyl group.

The alkaline metal ion represented by $m^+$ and Y, in general formulae (I) and (XVI) includes, for example, lithium ion, sodium ion, potassium ion, rubidium ion or cesium ion. Among them, for example, lithium ion, sodium ion or potassium ion is preferable.

The phosphonium ion represented by $m^+$ and Y includes, for example, alkylphosphonium ion having 1 to 3 carbon atoms such as tetramethylphosphonium ion, tetraethylphosphonium ion and tetra-n-propylphosphonium ion; for example, arylphosphonium ion such as tetraphenylphosphonium ion.

The alkyl group represented by $R^3$ in general formula (IV) may be any of straight chained, branched or cyclic group, and includes generally one having 1 to 6, preferably, 1 to 4 carbon atoms, and specifically, includes, for example, methyl group, ethyl group, n-propyl group, isopropyl group, n-butyl group, isobutyl group, sec-butyl group or tert-butyl group. Among them, n-butyl group is preferable.

Three $R^3$'s represented in general formula (IV) may be the same or the different, but the same one is preferable.

The alkaline earth metal ion represented by $M^{2+}$ in general formula (II) and (XVII) includes, for example, ions such as beryllium, magnesium, calcium, strontium and barium. Among them, for example, magnesium ion, calcium ion or barium ion is preferable.

The halogen atom represented by X includes, for example, fluorine atom, chlorine atom, bromine atom or iodine atom.

The alkoxide represented by X may be any of straight chained or branched group, and includes generally one having 1 to 4 carbon group, and specifically, includes, for example, methoxide, ethoxide, n-propoxide, isopropoxide, n-butoxide, isobutoxide, sec-butoxide or tert-butoxide.

Specific example of $MX^+$ in general formula (II) and (XVII) includes magnesium chloride cation or calcium chloride cation.

The alkaline earth metal ion represented by $M^{2+}$ in general formula (III) includes, for example, beryllium ion, magnesium ion, calcium ion, strontium ion or barium ion. Among them, magnesium ion, calcium ion or barium ion is preferable.

Specific example of methylene group which may have a substituent group, represented by A in general formulae (I) to (III) and (XVI) includes —$CH_2$—, —$CH(CH_3)$— or —$C(CH_3)_2$—. Among them, —$CH_2$— (methylene group) is preferable.

Three n's may be the same or the different, respectively, and generally, are 1 to 10, preferably, 1 or 2, respectively.

n pieces of A represented by $(A)_n$ may be the same or the different. Namely, for example, in the case of $(A)_2$ (n=2), specific example thereof includes, for example, $CH_2CH_2$, $CH(CH_3)CH(CH_3)$, $C(CH_3)_2CH_2$ or $C(CH_3)_2C(CH_2)_2$.

Compounds (1) to (35) are shown below as typical example of organic triol borate salt represented by general formula (I), but are not limited thereto.

It should be noted that, ones in which counter cations of the compounds (1) to (35) are exchanged to the corresponding counter cation of the compounds represented by general formula (II) or (III) become typical example of the compound represented by general formula (II) or (III), respectively.

[Formula 6]

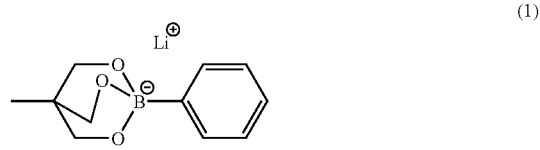

(1)

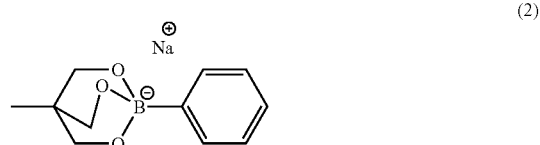

(2)

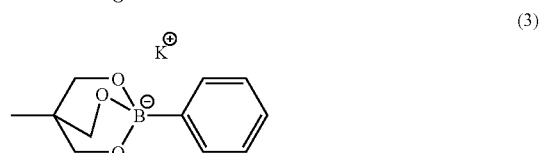

(3)

(4)

(5)

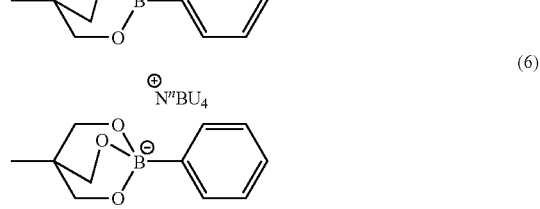

(6)

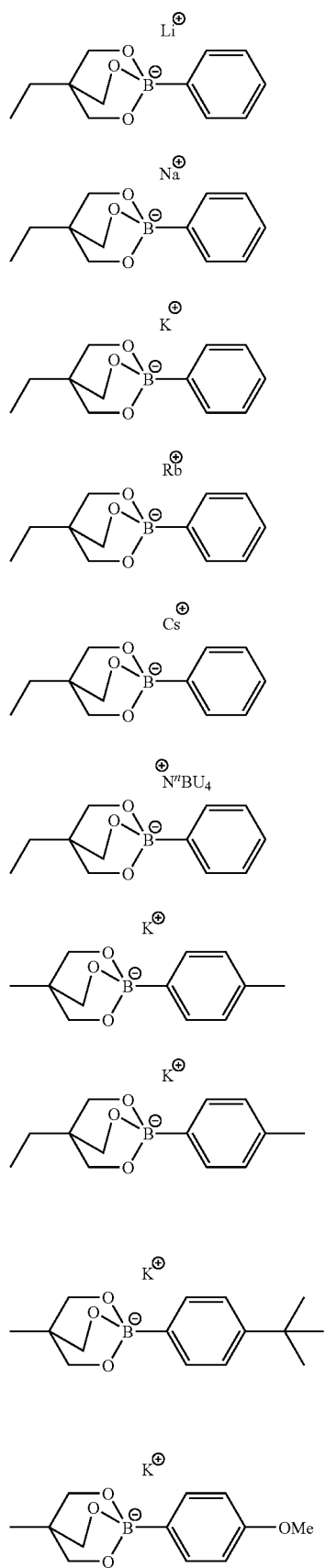
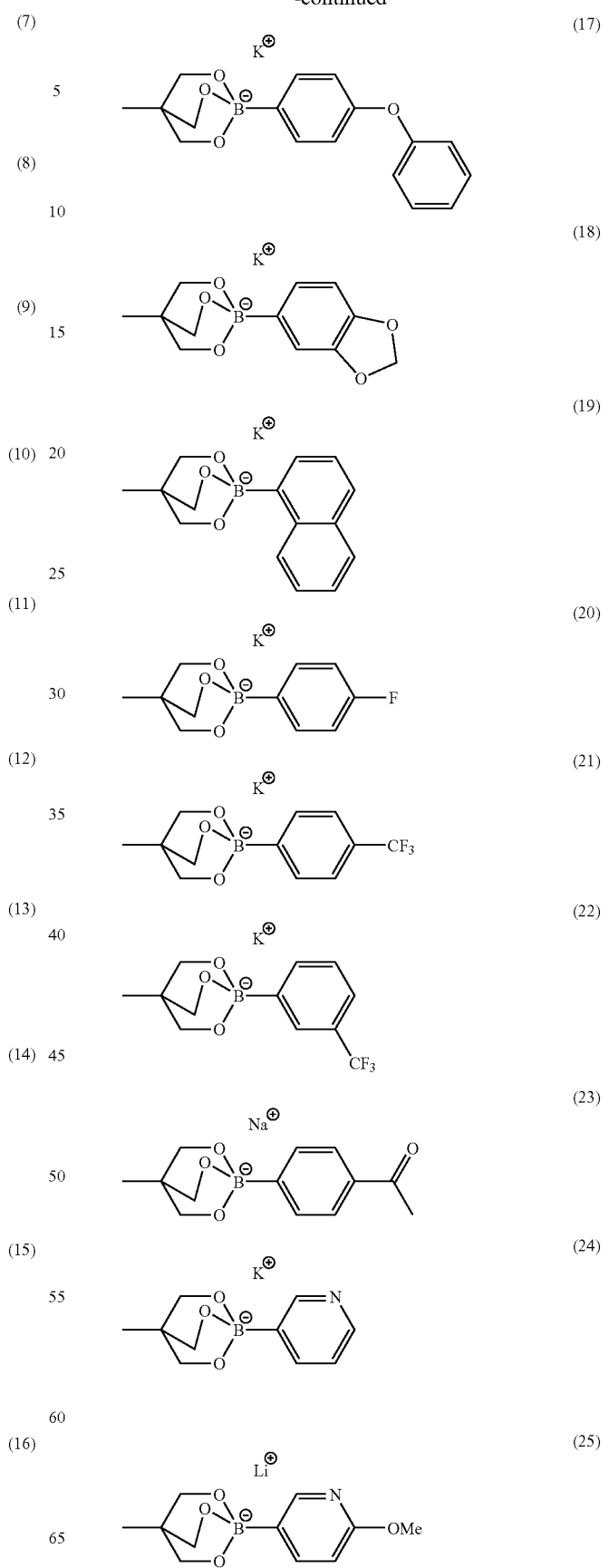

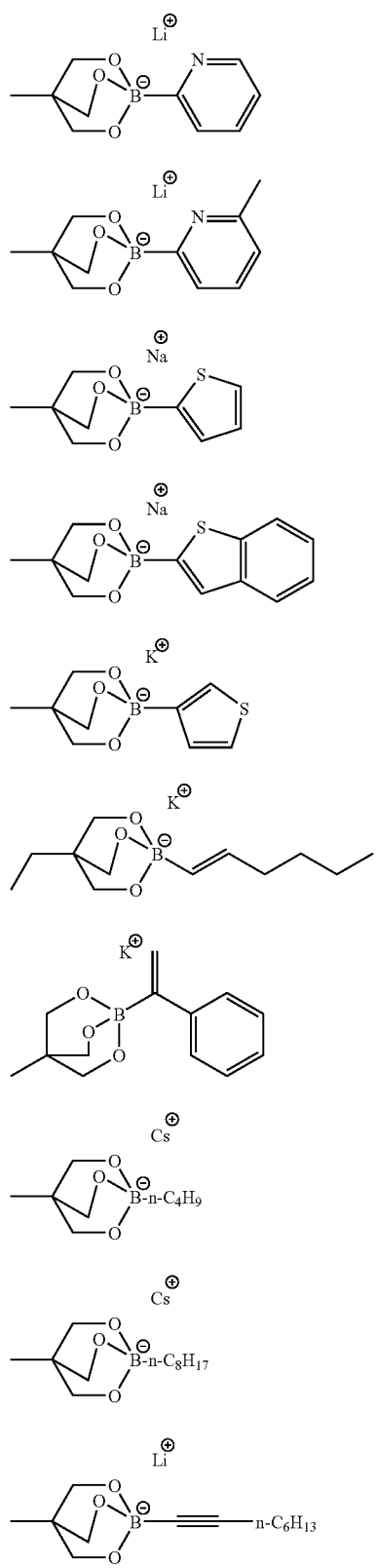

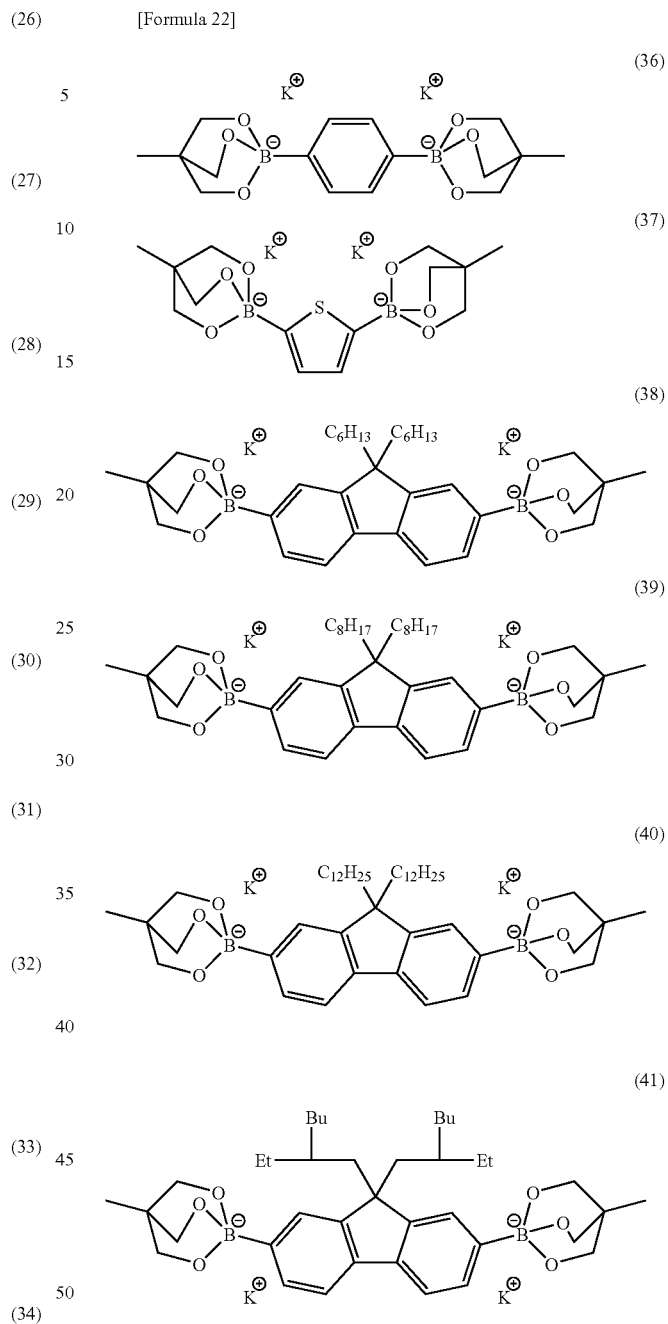

Compounds (36) to (41) are shown below as typical examples of organic triol borate salts represented by general formula (XVI), but are not limited thereto.

The production methods of organic triol borate salt represented by general formulae (I) to (III) according to the present invention include, for example, (1) The method that the corresponding organic boronic acid [$R^2B(OH)_2$, (wherein, $R^2$ is the same as the above described one)] is reacted with 0.1 to 1.5 times mole, preferably 0.9 to 1.1 times mole of triol [$R^1C[(A)_nOH]_3$ (wherein $R^1$, A and n are the same as the above described ones), relative to the said organic boronic acid in the reaction solvent, under heating reflux, and then, is reacted with 0.1 to 1.5 times mole, preferably 0.9 to 1.0 times mole of metallic hydroxide (mOH, $M(OH)_2$ (wherein m and M are the same as the above ones)] or metallic hydride [mH, $MH_2$ (wherein m and M are the same as the above ones)] relative to the said organic boronic acid;

(2) The method that the triol borate represented by general formula (XV):

[Formula 7]

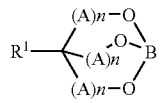
(XV)

(wherein, $R^1$, A and n are the same as the above described ones) is reacted with 0.1 to 1.5 times mole, preferably 0.9 to 1.1 times mole of organic metallic compound such as, for example, $R^1m$, $R^2MX$ (wherein $R^2$, m, M and X are the same as the above described ones), relative to the said triol borate in reaction solvent;

(3) The method that in the reaction solvent, the organic trialkoxy borate obtained from the reaction of the corresponding organic lithium compound or organic magnesium compound, and trimethyl borate or triisopropyl borate is reacted with 0.1 to 1.5 times mole, preferably 0.9 to 1.1 times mole of triol relative to the said organic trialkoxy borate;

Production method of organic triol borate salt represented by general formula (XVI) includes, for example, (4) The method that the corresponding organic boronic acid [$R^4(B(OH)_2)_2$ (wherein $R^4$ is the same as the above described one)] is reacted with 0.1 to 3 times mole, preferably, 1.8 to 2.2 times mole of triol [$R^1C[(A)_nOH]_3$ (wherein $R^1$, A and n are the same as the above described one), relative to the said organic boronic acid in reaction solvent under heating reflux, and then, is reacted with 1.8 to 2.0 times mole of metallic hydroxide [mOH, $M(OH)_2$ (wherein m and M are the same as the above described one)], or metallic hydride [mH, $MH_2$ (wherein m and M are the same as the above described one), relative to the said organic boronic acid;

(5) The method that the triol borate represented by general formula (VII) is reacted with 0.4 to 0.5 times mole of organic metallic compound such as, for example, $R^4(m)_2$, $R^4(MX)_2$ (wherein $R^4$, m, M and X are the same as the above described ones) relative to the said triol borate in reaction solvent;

(6) The method that in reaction solvent, organic trialkoxy borate obtained from the reaction of corresponding organic lithium compounds or organic magnesium compounds with trimethyl borate or triisopropyl borate is reacted with 1.8 to 2.2 times mole of triol relative to the said organic trialkoxy borate.

Accordingly, the organic triol borates of the present invention have not such a problem that conventional organic boronic acids have been needed to use more than theoretical amount thereof in reaction due to the formation of trimerization with dehydration, and, can carry out the desired reaction by using theoretical amount. Therefore, for example, when the reagent is expensive, it can be used efficiently.

Specific example of the above-described organic boronic acid [R2B(OH)2] includes, for example, methylboronic acid, ethylboronic acid, propylboronic acid, propenylboronic acid, isopropylboronic acid, butylboronic acid, butenylboronic acid, butynylboronic acid, isobutylboronic acid, sec-butylboronic acid, tert-butylboronic acid, pentylboronic acid, pentenylboronic acid, isopentylboronic acid, neopentylboronic acid, hexylboronic acid, hexenylboronic acid, hexynylboronic acid, heptylboronic acid, octylboronic acid, octynylboronic acid, nonylboronic acid, decylboronic acid, cyclopropylboronic acid, cyclopentylboronic acid, cyclohexylboronic acid, benzylboronic acid, phenylboronic acid, tolylboronic acid, tert-butylphenylboronic acid, methoxyphenylboronic acid, phenoxyphenylboronic acid, m-anisylboronic acid, xylylboronic acid, mesitylboronic acid, fluorophenylboronic acid, pentafluorophenylboronic acid, trifluorophenylboronic acid, acetylphenylboronic acid, biphenylboronic acid, thiophenylboronic acid, pyridylboronic acid, indenylboronic acid, naphthylboronic acid, furylboronic acid, thienylboronic acid, 3,4-methylenedioxyphenylboronic acid, 2-benzo[b]thienylboronic acid, 6-methyl-2-pyridineboronic acid, 6-methoxy-3-pyridineboronic acid or α-phenylvinylboronic acid.

Specific example of the above-described metal hydroxide [mOH, $M(OH)_2$] includes, for example, alkaline metal hydroxide such as lithium hydroxide, sodium hydroxide, potassium hydroxide, cesium hydroxide and rubidium hydroxide; for example, alkaline earth metal hydroxide such as magnesium hydroxide, calcium hydroxide, strontium hydroxide and barium hydroxide.

Specific example of the above-described metal hydride [mH, $MH_2$] includes, for example, alkaline metal hydrides such as lithium hydride, sodium hydride and potassium hydride.

Specific example of triol borate represented by general formula (XV) includes, for example, 4-methyl-2,6,7-trioxa-1-borabicyclo[2.2.2]octane, 4-ethyl-2,6,7-trioxa-1-borabicyclo[2.2.2]octane and 4-tert-butyl-2,6,7-trioxa-1-borabicyclo[2.2.2]octane.

Specific example of organic lithium compound includes, for example, methyl lithium, ethyl lithium, propyl lithium, propenyl lithium, isopropyl lithium, butyl lithium, butenyl lithium, butynyl lithium, isobutyl lithium, sec-butyl lithium, tert-butyl lithium, pentyl lithium, pentenyl lithium, isopentyl lithium, neopentyl lithium, hexyl lithium, hexenyl lithium, hexynyl lithium, heptyl lithium, octyl lithium, nonyl lithium, decyl lithium, cyclopropyl lithium, cyclopentyl lithium, cyclohexyl lithium, benzyl lithium, phenyl lithium, tolyl lithium, m-anisyl lithium, xylyl lithium, mesityl lithium, pentafluorophenyl lithium, biphenyl lithium, thiophenyl lithium, pyridyl lithium, indenyl lithium, naphthyl lithium and furyl lithium.

Specific example of organic magnesium compound, includes, for example, methyl magnesium iodide, ethyl magnesium iodide, propyl magnesium iodide, propenyl magnesium bromide, isopropyl magnesium bromide, butyl magnesium bromide, butenyl magnesium bromide, butynyl magnesium iodide, isobutyl magnesium chloride, sec-butyl magnesium chloride, t-butyl magnesium bromide, pentyl magnesium bromide, pentenyl magnesium bromide, isopentyl magnesium bromide, neopentyl magnesium chloride, hexyl magnesium chloride, hexenyl magnesium bromide, hexynyl magnesium iodide, heptyl magnesium chloride, octyl magnesium chloride, nonyl magnesium chloride, decyl magnesium chloride, cyclopropyl magnesium bromide, cyclopentyl magnesium bromide, cyclohexyl magnesium bromide, benzyl magnesium chloride, phenyl magnesium bromide, tolyl magnesium chloride, m-anisyl magnesium chloride, xylyl magnesium chloride, mesityl magnesium chloride, pentafluorophenyl magnesium chloride, biphenyl magnesium chloride, thiophenyl magnesium chloride, pyridyl magnesium bromide, indenyl magnesium chloride, naphthyl magnesium chloride and furyl magnesium chloride.

The reaction solvent to be used in production methods (1) to (3) of the organic triol borate salt of the present invention is not particularly limited as long as it is inert to raw materials for reaction and reaction products, and includes, for example, hydrocarbons such as n-hexane, n-heptane and cyclohexane; for example, aromatic hydrocarbons such as benzene, toluene and xylene; for example, ethers such as diethyl ether, dimethoxyethane, diethoxyethane, tetrahydrofuran and cyclopentyl methyl ether. These may be used alone or in combination of two or more kinds. In addition, reaction selectivity can be changed depending on reaction solvent to be used and combination thereof.

The reaction temperature when the organic triol borate salt is produced may be selected, generally, from the range of $-100°$ C. to $200°$ C. appropriately, for example, in the case of the above-described method (1), preferably, 50 to $150°$ C., in the case of the above-described method (2), preferably, $-80$ to $100°$ C.

When the reaction time is the same time until consuming the raw material to be used and forming the desired organic triol borate, there is no problem, it is generally 3 to 24 hours.

The organic trial borate salt of the present invention have advantages, for example, that synthesis thereof can be carried out under mild temperature condition, trimerization with dehydration is not occurred, and activation by base is not needed. Therefore, they can be used as stable and high active organic boron reagents, namely, the reagents for organic synthesis reaction (more specifically, for example, cross coupling reaction, addition reaction, etc.) such as carbon-carbon bond formation reaction, carbon-nitrogen bond formation reaction, carbon-oxygen bond formation reaction, carbon-sulfur bond formation reaction.

The reagents for organic synthesis reaction containing organic triol borate salt in the present invention, when they are used as reactants, can be preferably used for all the reaction of carbon-carbon bond formation reaction, carbon-nitrogen bond formation reaction, carbon-oxygen bond formation reaction, carbon-sulfur bond formation reaction, for example, such as cross coupling reaction and addition reaction, besides, for example, conventional organic boronic acid reagent may be used, and specific reaction example thereof includes cross coupling reaction by palladium catalyst, addition reaction by rhodium catalyst, amination reaction by copper catalyst, etherification reaction by copper catalyst.

Reaction can be performed smoothly by using the reagents for organic synthesis reaction of the present invention without additives except catalyst The above-described various organic synthesis reactions may be carried out, if necessary, in reaction solvent, by reacting organic triol borate salt of the present invention with the corresponding reaction substrate in the presence of catalyst.

The catalysts to be used in the said reaction includes, for example, iron catalyst, ruthenium catalyst, osmium catalyst, nickel catalyst, palladium catalyst, platinum catalyst, cobalt catalyst, rhodium catalyst, iridium catalyst, copper catalyst, silver catalyst or gold catalyst.

The iron catalyst includes one in which iron valence is 0 to 3, preferably 3.

The ruthenium catalyst includes one in which valence of ruthenium atom is generally 0 to 2, preferably 0.

The osmium catalyst includes one in which osmium valence is generally 0 to 3, preferably 2.

The nickel catalyst includes one in which valence of nickel atom is generally 0 to 2, preferably 0.

The palladium catalyst includes one in which palladium valence is 0 to 4, preferably 0.

The platinum catalyst includes one in which valence of platinum atom is generally 0 to 4, preferably 0.

The cobalt catalyst includes one in which valence of cobalt atom is generally 0 or 1, preferably 1.

The rhodium catalyst includes one in which valence of rhodium atom is generally 0 or 1, preferably 0.

The iridium catalyst includes one in which valence of iridium is generally 0 to 5, preferably 1 to 3, more preferably 3.

The copper catalyst includes one in which valence of copper atom is generally 0 to 2, preferably 1.

The silver catalyst includes one in which valence of silver is generally 0 to 2, preferably 1.

The gold catalyst includes one in which valence of gold is generally 0 to 2, preferably 1.

The above-described catalysts may be a metal alone such as iron, ruthenium, osmium, nickel, palladium, platinum, cobalt, rhodium, iridium, copper, silver and gold; or oxide, halide or acetate of their metals; or coordinated one with ligand, in addition, the catalysts in which metal, metal oxide, metal halide, metal acetate, or metal complex is supported by various carriers may be used. Hereinafter, the catalyst supported by carrier may be abbreviated as "carrier supported metallic catalyst", and catalyst without supporting by carrier may be abbreviated as "metallic catalyst".

Among the catalyst to be used in organic synthesis reaction of the present invention, the ligand of a metal catalyst, which may be coordinated with a ligand, includes, for example, organic phosphine ligand such as triphenylphosphine (PPh3), bis(diphenylphosphino)methane (Ph2PCH2PPh2), 1,2-bis (diphenylphosphino)ethane (Ph2PCH2CH2PPh2), 1,3-bis (diphenylphosphino)propane (Ph2PCH2CH2CH2PPh2), 1,4-bis(diphenylphosphino)butane (Ph2PCH2CH2CH2CH2PPh2), PMe2Ph, P(Ome)2Ph, P(Ome)Ph2, P(Ome)$_3$, Pet2Ph, P(Oet)2Ph, P(Oet)Ph2, P(Oet)3, Me2PCH2CH2CH2Pme2, 1,5-cyclooctadiene (COD), dibenzylidene acetone (DBA), bipyridine (BPY), phenanthroline (PHE), benzonitrile (PhCN), isocyanide (RNC), triethylarsine (As(Et)3), acetylacetonato (acac), pentamethylcyclopentadienyl (Cp*), dimethylphenylphosphine (P(CH3)2Ph), diphenylphosphino ferrocene (DPPF), trimethylphosphine (P(CH3)3), triethylphosphine (Pet3), tri-tert-butylphosphine (PtBu3), tricyclohexylphosphine (Pcy3), trimethoxyphosphine (P(OCH3)3), triethoxyphosphine (P(Oet)3), tri-tert-butoxyphosphine (P(OtBu)3), triphenoxyphosphine (P(Oph)3) and tri o-tolylphosphine (P(o-tolyl)3); for example, 2,2'-bipyridine, 1,5-cyclooctadiene, norbornadiene, cyclopentadienyl ligand (C5H5), carbon mono-oxide or tetrahydrofuran.

Specific example of the palladium metal catalyst includes, for example, Pd; for example, palladium hydroxide catalyst such as Pd(OH)$_2$; for example, palladium oxide catalyst such as PdO; for example, palladium halide catalyst such as PdBr$_2$, PdCl$_2$ and PdI$_2$; for example, palladium acetate catalyst such as palladium acetate (Pd(OAc) 2) and palladium trifluoroacetate (Pd (OCOCF$_3$)$_2$); for example palladium metal complex catalyst coordinated with ligand such as Pd(RNC)$_2$Cl$_2$, Pd(acac)$_2$/diacetate bis(triphenylphosphine) palladium [Pd (OAc)$_2$ (PPh$_3$)$_2$], Pd (PPh$_3$)$_4$, Pd$_2$(dba)$_3$, Pd(NH$_3$)$_2$Cl$_2$, Pd(CH$_3$CN)$_2$Cl$_2$, dichlorobis(benzonitrile)palladium [Pd (PhCN)$_2$Cl$_2$], Pd(dppe)Cl$_2$, Pd(dppf)Cl$_2$, Pd(PCy$_3$)$_2$Cl$_2$, Pd(PPh$_3$)$_2$Cl$_2$, Pd[P(o-tolyl)$_3$]$_2$Cl$_2$, Pd(cod)$_2$Cl$_2$ and Pd(PPh$_3$) (CH$_3$CN)$_2$Cl$_2$.

Specific example of platinum metal catalyst include, for example, Pt; for example, platinum oxide catalyst such as PtO$_2$; for example, platinum halide catalyst such as PtCl$_4$, PtCl$_2$ and K$_2$PtCl$_4$; for example, platinum metal complex catalyst coordinated with ligand such as PtCl$_2$(cod), PtCl$_2$ (dba), PtCl$_2$(Pcy$_3$)$_2$, PtCl$_2$ (P(OEt)$_3$)$_2$, PtCl$_2$ (P(O$^t$Bu)$_3$)$_2$, PtCl$_2$(bpy), PtCl$_2$(phe), Pt(PPh$_3$)$_4$, Pt(cod)$_2$, Pt(dba)$_2$, Pt(bpy)$_2$ and Pt (phe)$_2$.

Specific example of rhodium metal catalyst includes, for example, Rh; for example, rhodium metal complex catalyst coordinated with the ligand such as RhCl(PPh$_3$)$_3$, [Rh(coe)$_2$Cl]$_2$ and [Rh(nbd)((R)-binap)]BF$_4$.

Specific example of iridium metal catalyst includes, for example, Ir; for example, iridium metal complex catalyst coordinated with the ligand such as Ir(cod)(acac) and Cp*Ir(P(CH$_3$)$_3$)$_3$)Cl$_2$.

Specific example of ruthenium metal catalyst includes, for example, Ru; for example, ruthenium metal complex catalyst coordinated with the ligand such as RuCl$_2$(PPh$_3$)$_3$.

Specific example of nickel metal catalyst includes, for example, Ni; for example, nickel oxide catalyst such as NiO; for example, nickel halide catalyst such as NiCl$_2$; for example, nickel metal complex catalyst coordinated with the ligand such as NiCl$_2$(dppe), NiCl$_2$(PPh$_3$)$_2$, Ni(PPh$_3$)$_4$, Ni(P(OPh)$_3$)$_4$ and Ni(cod)$_2$.

Specific example of cobalt metal catalyst includes, for example, cobalt metal complex catalyst coordinated with the ligand such as Co(C$_3$H$_5$){P(OCH$_3$)$_3$}$_3$.

The carrier, wherein the above-described metal catalyst is supported on the carrier, includes, for example, carbon, alumina, silica gel, zeolite, molecular sieve, ion exchange resin or polymer.

These catalysts may be used alone or in arbitrary combination of two or more kinds.

Usage of the catalyst to be used in organic synthesis reaction of the present invention, in spite of whether it is supported by carrier or not, is generally so-called catalytic amount, and then preferably in sequence 0.01 to 80% by weight, 0.01 to 50% by weight, 0.01 to 20% by weight, relative to the organic triol borate salt to be used as substrate of reaction, and also, amount of catalyst metal contained in the catalyst as a whole is 0.0005% by weight to 20% by weight.

Reaction temperature in the organic synthesis reaction of the present invention is generally 10° C. to 300° C., preferably 20 to 180° C.

Reaction time in the organic synthesis reaction of the present invention is generally 30 minutes to 100 hours, preferably 1 to 50 hours, more preferably 1 to 30 hours, further preferably 3 to 30 hours.

Case, in which coupling reaction by palladium catalyst is carried out with using the reagent for the organic synthesis reaction containing the said organic triol borate salt of the present invention, is explained as an example.

Namely, for example, the said organic triol borate salt (substrate), 0.1 to 3 times mole, preferably 0.5 to 2 times mole of organic halides relative to said substrate, and 0.01 to 80% by weight of palladium catalyst relative to said substrate (0.0005 to 20% by weight of palladium metal relative) to said substrate are added into reaction solvent (amount of 1 to 20,000 equivalent, preferably 10 to 700 equivalent, relative to the catalyst), and are reacted by stirring at about 20° C. to 200° C., in about 30 minutes to 100 hours to obtain the objects.

In addition, case, in which 1,4-addition reaction by rhodium catalyst is carried out with using the reagent for the organic synthesis reaction containing the relevant organic triol borate salt of the present invention, is explained as an example.

Namely, for example, the said organic triol borate salt (substrate), 0.1 to 3 times mole, preferably 0.5 to 2 times mole of the electron-withdrawing group substituted olefin compound relative to said substrate, and 0.01 to 80% by weight of rhodium catalyst relative to said substrate (0.0005 to 20% by weight of rhodium metal relative to said substrate) are added into reaction solvent (amount of 1 to 20,000 equivalent, preferably 10 to 700 equivalent relative to the catalyst) and are reacted by stirring at about 20° C. to 200° C., for about 30 minutes to 100 hours to obtain the objects.

In addition, case, in which amination reaction by copper catalyst is carried out with using the reagent for the organic synthesis reaction containing the relevant organic triol borate salt of the present invention, is explained as an example.

Namely, for example, the organic triol borate salt (substrate), 0.1 to 3 times mole, preferably 0.5 to 2 times mole of amine compound, relative to said substrate, and 0.01 to 80% by weight of copper catalyst relative to said substrate (0.0005 to 20% by weight of copper metal relative to said substrate) are added in the reaction solvent (amount of 1 to 20,000 equivalent, preferably 10 to 700 equivalent, relative to catalyst), after replacing the atmosphere with oxygen in reaction system, they are reacted by stirring at about 20° C. to 200° C., for about 30 minutes to 100 hours to obtain the objects.

In addition, when etherification reaction is carried out with using the reagent for the organic synthesis reaction containing the relevant organic triol borate salt of the present invention, by carrying out in a manner similar to the amination reaction by copper catalyst except using various alcohols instead of amine compounds, the object can be obtained.

Further, when thioetherification reaction is carried out with using the reagent for the organic synthesis reaction containing the said organic triol borate salt of the present invention, by carrying out in a manner similar to the amination reaction by copper catalyst except using various thio alcohols instead of amine compounds, the object can be obtained.

Namely, for example, the said organic triol borate salt (substrate), 0.1 to 3 times mole, preferably 0.5 to 2 times mole of amine compound, relative to said substrate, and 0.01 to 80% by weight of copper catalyst relative to said substrate (0.0005 to 20% by weight of copper metal relative to said substrate) are added in the reaction solvent (amount of 1 to 20,000 equivalent, preferably 10 to 700 equivalent, relative to catalyst), after replacing the atmosphere with oxygen in reaction system, they are reacted by stirring at about 20° C. to 200° C., for about 30 minutes to 100 hours to obtain the objects.

When, for example, carbon-carbon bond formation reaction, carbon-nitrogen bond formation reaction, carbon-oxygen bond formation reaction or carbon-sulfur bond formation reaction, such as cross coupling reaction and 1,4-addition reaction are carried out by using the organic triol borate salt of the present invention, the reaction in anhydrous organic solvent becomes possible, therefore, when this is used as the reagent for organic synthesis reaction such as, for example, cross coupling reaction and 1,4-addition reaction, the reaction can be carried out efficiently. In particular, conventional reagents cannot be practically used as reagent for coupling reaction such as, for example, pyridylation reaction because C—B bond is broken easily according to hydrolysis. However, by using the organic triol borate salt of the present invention corresponding to, for example, hetero-ring boronic acid such as 2-pyridine boronic acid, 2-thiophene boronic acid, 2-pyrrole boronic acid and 2-furan boronic acid; for example, alkynyl boronic acid such as 2-octynylboronic acid, cross coupling reaction such as pyridylation can be efficiently carried out.

The present invention will be described in detail herein below by Examples, but not limited thereto.

It should be noted that, Examples 1 to 36 and Examples 46 to 51 are demonstrated as synthesis examples of organic triol borate salts, and Examples 37 to 45 are demonstrated as reaction examples using organic triol borate salt.

Example 1

The solution of phenylboronic acid (100 mmol) and 1,1,1-tris(hydroxymethyl)ethane (100 mmol) in toluene (200 ml)

was heated under reflux for 4 hours, and was extracted with ethyl acetate. Then, solvent was removed, potassium hydroxide (90 mmol) was added to the resulting solid in toluene solution, further, was heated under reflux for 4 hours. After cooling to room temperature, this was filtrated, and the resulting solid was dried under reduced pressure. Yield of product was 83%. Product was identified as phenyl triol borate potassium salt (compound (3), formula (V)).

[Physical Property Data]

$^1$H-NMR (DMSO-$d_6$, 400 MHz) δ: 0.47 (s, 3H), 3.56 (s, 6H), 6.88-6.98 (m, 3H), 7.30 (d, J=6.8 Hz, 2H); $^{13}$C-NMR (DMSO-$d_6$, 100 MHz) δ: 16.5, 73.9, 124.2, 125.7, 132.3; $^{11}$B-NMR (DMSO-$d_6$, 128 MHz) δ: 4.39; MS (m/z) 56(5), 104(100), 148(27), 205(10, M$^+$); exact mass calcd for $C_{11}H_{14}BO_3$: 205.1036; found 205.1041; anal. calcd for $C_{11}H_{14}BKO_3$: C, 54.12, H, 5.78; found C, 52.76, H, 5.65.

[Formula 8]

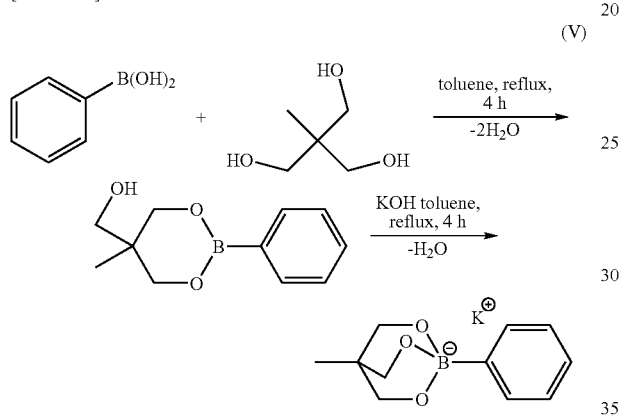

(V)

Example 2

Into the solution of phenylboronic acid (100 mmol) and 1,1,1-tris(hydroxymethyl)ethane (120 mmol) in ether (200 ml), anhydrous magnesium sulfate (20 g) was added, and was stirred for 24 hours at 25° C. The solution was extracted by adding water and ethyl acetate, dried with magnesium sulfate, and followed by removing the solvent to obtain phenylboronic acid triol ester. NMR chemical shift of this ester was shown as follows:

[Physical Property Data]

$^1$H-NMR. (DMSO-$d_6$, 400 MHz) δ: 0.87 (s, 3H), 3.33 (d, J=4.9 Hz, 2H), 3.75 (d, J=10.3 Hz, 2H), 3.75 (d, J=10.7 Hz, 2H), 4.85 (t, J=4.9 Hz, 1H), 7.31-7.44 (m, 3H), 7.68 (d, J=7.8 Hz, 2H); $^{13}$C-NMR (DMSO-$d_6$, 100 MHz): δ: 17.4, 36.7, 63.1, 67.7, 127.8, 130.9, 133.7; $^{11}$B-NMR (DMSO-$d_6$, 128 MHz) δ: 30.1; MS (m/z) 43(14), 57(36), 72(39), 78(16), 91(14), 105(100), 117(55), 122(38), 132(43), 151(17), 159 (15), 173(35), 188(16), 206 (83, M$^+$); exact mass calcd for $C_{11}H_{15}BO_3$: 206.1114; found 206.1102.

Next, the solution of the above-described ester and sodium hydride in ether was stirred at 25° C. for 24 hours to obtain the object in 90% yield. The object was identified as phenyl triol borate sodium salt (compound (2), formula (VI)). NMR chemical shift of this ester was shown as follows:

[Physical Property Data]

$^1$H-NMR (DMSO-$d_6$, 400 MHz) δ: 0.47 (s, 3H), 3.57 (s, 6H), 6.88-6.98 (m, 3H), 7.30 (d, J=6.8 Hz, 2H); $^{13}$C-NMR (DMSO-$d_6$, 100 MHz) δ: 16.5, 34.6, 73.9, 124.2, 125.7, 132.3; $^{11}$B-NMR (DMSO-$d_6$, 128 MHz) δ: 8.84

[Formula 9]

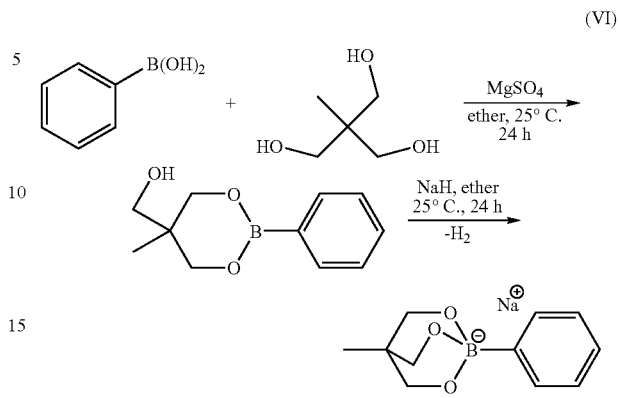

(VI)

Example 3

Into the solution of triol borate (100 mmol) in THF (200 ml), phenyl Grignard solution was added dropwise at −78° C., and stirred for 1 hour as it was. Temperature of the reaction mixture was elevated to 25° C., and stirred for 1 hour. Into toluene solution of the solid obtained by removing the solvent after extraction, potassium hydroxide (90 mmol) was added, and heated under reflux for 4 hours. After cooling to room temperature, the solution was filtered, and the resulting solid was dried under reduced pressure. Yield of product was 63%. Product was identified as phenyl triol borate potassium salt (compound (3), formula (VII)).

[Formula 10]

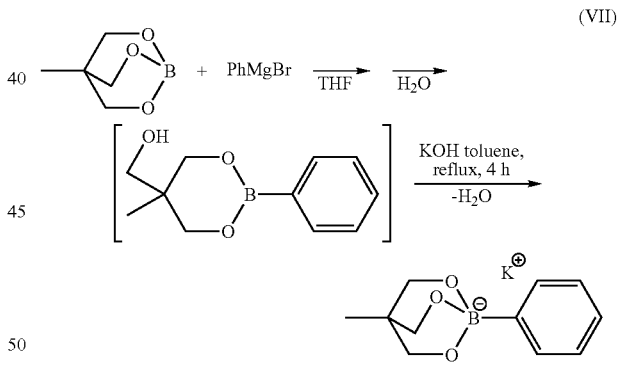

(VII)

Example 4

Into the solution of phenyl lithium (100 mmol) in THF (200 ml), trimethyl borate (110 mmol) was added dropwise at −78° C. After elevating to room temperature, solution of 1,1,1-tris(hydroxymethyl)ethane (100 mmol) in THF (150 ml) was added, and stirred for 5 hours as it was. After removing the solvent and drying, the object was obtained (yield: 52%, compound (1), formula (VIII)).

[Physical Property Data]

$^1$H-NMR (DMSO-$d_6$, 400 MHz) δ: 0.46 (s, 3H), 3.55 (s, 6H), 6.86-6.97 (m, 3H), 7.29 (d, J=6.4 Hz, 2H); $^{13}$C-NMR (DMSO-$d_6$, 100 MHz) δ: 16.5, 34.7, 74.0, 124.1, 125.6, 132.4; $^{11}$B-NMR (DMSO-$d_6$, 128 MHz) δ: 3.94

[Formula 11]

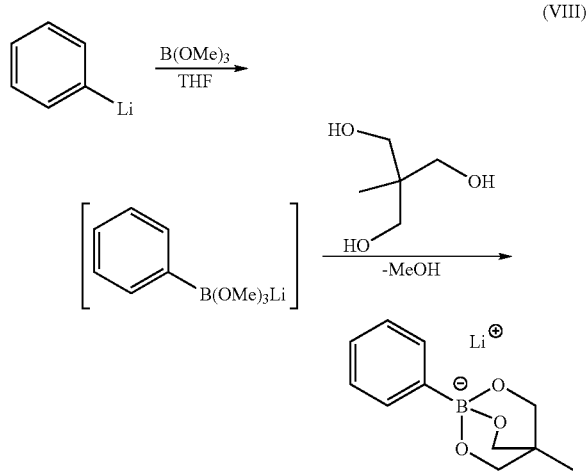

Example 5

Into the solution of 2-bromopyridine (100 mmol) in THF (400 ml), solution of n-butyllithium in hexane (110 mmol) was added dropwise, stirred for 1 hours. After adding triisopropyl borate (120 mmol) to reaction mixture, solution was stirred at −78° C. for 2 hours. After elevating to room temperature, solution of 1,1,1-tris(hydroxymethyl)ethane (100 mmol) in THF (150 ml) was added, and stirred for 5 hours as it was. Solvent was removed and the residue was dried to obtain the object (yield: 82%, compound (26), formula (IX)).

[Physical Property Data]
$^1$H-NMR (DMSO-$d_6$, 400 MHz) δ: 0.54 (s, 3H), 3.67 (s, 6H), 7.06-7.51 (m, 3H), 8.24 (br s, 2H); $^{13}$C-NMR (DMSO-$d_6$, 100 MHz) δ: 15.9, 73.5, 120.8, 127.8, 134.4, 146.9; $^{11}$B-NMR (DMSO-$d_6$, 128 MHz) δ: 3.25

[Formula 12]

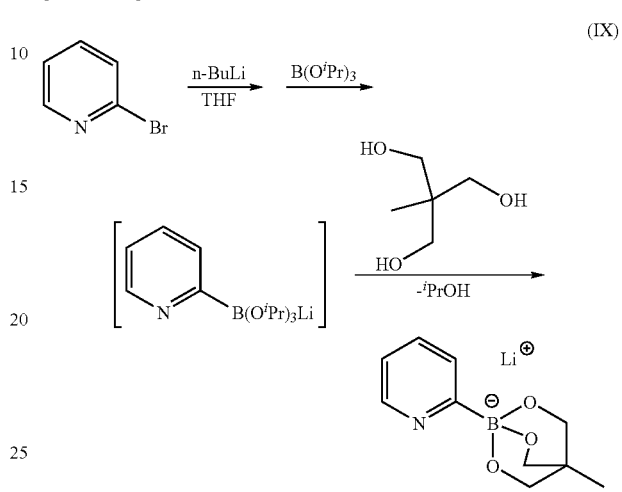

Examples 6 to 36

By carrying out a similar manner to any of Example 1, 2 and 5 except using the compounds described in Table-1 instead of phenylboronic acid, 1,1,1-tris(hydroxymethyl) ethane and/or potassium hydroxide, the objects were obtained. These results were additionally shown in Table-1.

TABLE 1

|  | Compound | Synthetic Method | Organic boronic acid | Triol | Additive | Yield (%) |
|---|---|---|---|---|---|---|
| Exam. 6 | (4) | Exam. 1 | Phenyl boronic acid | 1,1,1-tris(hydroxymethyl)ethane | RbOH | 88 |
| Exam. 7 | (5) | Exam. 1 | Phenyl boronic acid | 1,1,1-tris(hydroxymethyl)ethane | CsOH | 89 |
| Exam. 8 | (6) | Exam. 1 | Phenyl boronic acid | 1,1,1-tris(hydroxymethyl)ethane | N(nBu)$_4$OH | 76 |
| Exam. 9 | (7) | Exam. 1 | Phenyl boronic acid | 1,1,1-tris(hydroxymethyl)propane | LiOH | 71 |
| Exam. 10 | (8) | Exam. 1 | Phenyl boronic acid | 1,1,1-tris(hydroxymethyl)propane | NaOH | 78 |
| Exam. 11 | (9) | Exam. 1 | Phenyl boronic acid | 1,1,1-tris(hydroxymethyl)propane | KOH | 84 |
| Exam. 12 | (10) | Exam. 1 | Phenyl boronic acid | 1,1,1-tris(hydroxymethyl)propane | RbOH | 85 |
| Exam. 13 | (11) | Exam. 1 | Phenyl boronic acid | 1,1,1-tris(hydroxymethyl)propane | CsOH | 87 |
| Exam. 14 | (12) | Exam. 1 | Phenyl boronic acid | 1,1,1-tris(hydroxymethyl)propane | N(nBu)$_4$OH | 83 |
| Exam. 15 | (13) | Exam. 1 | p-tolyl boronic acid | 1,1,1-tris(hydroxymethyl)ethane | KOH | 84 |
| Exam. 16 | (14) | Exam. 1 | p-tolyl boronic acid | 1,1,1-tris(hydroxymethyl)propane | KOH | 84 |
| Exam. 17 | (15) | Exam. 1 | p-tert-butyl phenyl boronic acid | 1,1,1-tris(hydroxymethyl)ethane | KOH | 75 |
| Exam. 18 | (16) | Exam. 1 | p-methoxy phenyl boronic acid | 1,1,1-tris(hydroxymethyl)ethane | KOH | 35 |
| Exam. 19 | (17) | Exam. 1 | p-phenoxy phenyl boronic acid | 1,1,1-tris(hydroxymethyl)ethane | KOH | 51 |

TABLE 1-continued

| | Compound | Synthetic Method | Organic boronic acid | Triol | Additive | Yield (%) |
|---|---|---|---|---|---|---|
| Exam. 20 | (18) | Exam. 1 | 3,4-methylene dioxyphenyl boronic acid | 1,1,1-tris(hydroxymethyl)ethane | KOH | 83 |
| Exam. 21 | (19) | Exam. 1 | 1-naphthalene boronic acid | 1,1,1-tris(hydroxymethyl)ethane | KOH | 43 |
| Exam. 22 | (20) | Exam. 1 | p-fluoro phenyl boronic acid | 1,1,1-tris(hydroxymethyl)ethane | KOH | 83 |
| Exam. 23 | (21) | Exam. 1 | p-trifluoro phenyl boronic acid | 1,1,1-tris(hydroxymethyl)ethane | KOH | 79 |
| Exam. 24 | (22) | Exam. 1 | m-trifluoro phenyl boronic acid | 1,1,1-tris(hydroxymethyl)ethane | KOH | 18 |
| Exam. 25 | (23) | Exam. 2 | 4-acetyl phenyl boronic acid | 1,1,1-tris(hydroxymethyl)ethane | NaH | 50 |
| Exam. 26 | (24) | Exam. 1 | 3-pyridine boronic acid | 1,1,1-tris(hydroxymethyl)ethane | KOH | 27 |
| Exam. 27 | (25) | Exam. 5 | 6-methoxy-3-pyridyl boronic acid | 1,1,1-tris(hydroxymethyl)ethane | n-BuLi/B(Oi-Pr)$_3$ | 99 |
| Exam. 28 | (27) | Exam. 5 | 6-methyl-2-pyridyl boronic acid | 1,1,1-tris(hydroxymethyl)ethane | n-BuLi/B(Oi-Pr)$_3$ | 95 |
| Exam. 29 | (28) | Exam. 5 | 2-thiophene boronic acid | 1,1,1-tris(hydroxymethyl)ethane | n-BuLi/B(Oi-Pr)$_3$ | 99 |
| Exam. 30 | (29) | Exam. 2 | 2-benzo[b]thiophene boronic acid | 1,1,1-tris(hydroxymethyl)ethane | NaH | 51 |
| Exam. 31 | (30) | Exam. 1 | 3-thiophene boronic acid | 1,1,1-tris(hydroxymethyl)ethane | KOH | 66 |
| Exam. 32 | (30) | Exam. 1 | 1-hexenyl boronic acid | 1,1,1-tris(hydroxymethyl)propane | KOH | 67 |
| Exam. 33 | (32) | Exam. 1 | 1-phenyl vinyl boronic acid | 1,1,1-tris(hydroxymethyl)ethane | KOH | 40 |
| Exam. 34 | (33) | Exam. 1 | n-butyl boronic acid | 1,1,1-tris(hydroxymethyl)ethane | CsOH | 73 |
| Exam. 35 | (34) | Exam. 1 | n-octyl boronic acid | 1,1,1-tris(hydroxymethyl)ethane | CsOH | 73 |
| Exam. 36 | (25) | Exam. 5 | 1-octynyl boronic acid | 1,1,1-tris(hydroxymethyl)ethane | n-BuLi/B(Oi-Pr)$_3$ | 57 |

It should be noted that, physical property data of organic triol borate salt of the present invention obtained from examples to 25 and 27 to 36 are as follows:

Compound (4): $^1$H NMR (DMSO-d$_6$, 400 MHz) δ: 0.47 (s, 3H), 3.57 (s, 6H), 6.89-6.99 (m, 3H), 7.30 (d, J=6.8 Hz, 2H); $^{13}$C NMR (DMSO-d$_6$, 100 MHz) δ: 16.5, 34.6, 73.9, 124.2, 125.8, 132.3; $^{11}$B NMR (DMSO-d$_6$, 128 MHz) δ: 4.23

Compound (5): $^1$H NMR (DMSO-d$_6$, 400 MHz) δ: 0.47 (s, 3H), 3.56 (s, 6H), 6.87-6.98 (m, 3H), 7.30 (d, J=6.8 Hz, 2H); $^{13}$C NMR (DMSO-d$_6$, 100 MHz) δ: 16.5, 34.6, 73.9, 124.2, 125.7, 132.3; $^{11}$B NMR (DMSO-d$_6$, 128 MHz) δ: 4.02

Compound (6): $^1$H NMR (DMSO-d$_6$, 400 MHz) δ: 0.46 (s, 3H), 0.92 (t, J=7.3 Hz, 12H), 1.28 (m, 8H), 1.53 (m, 8H), 3.13 (m, 8h), 3.56 (s, 6H), 6.87-6.97 (m, 3H), 7.30 (d, J=6.8 Hz, 2H); $^{13}$C NMR (DMSO-d$_6$, 100 MHz) δ: 13.7, 16.5, 19.4, 23.2, 34.7, 57.6, 73.7, 124.2, 125.6, 132.4; $^{11}$B NMR (DMSO-d$_6$, 128 MHz) δ: 4.36

Compound (7): $^1$H NMR (DMSO-d$_6$, 400 MHz) δ: 0.69 (t, J=7.6 Hz, 3H), 0.93 (q, J=7.6 Hz, 2H), 3.56 (s, 6H), 6.86-6.97 (m, 3H), 7.29 (d, J=7.8 Hz, 2H); $^{13}$C NMR (DMSO-d$_6$, 100 MHz) δ: 8.29, 24.3, 36.7, 71.8, 124.0, 125.6, 132.4; $^{11}$B NMR (DMSO-d$_6$, 128 MHz) δ: 4.07

Compound (8): $^1$H NMR (DMSO-d$_6$, 400 MHz) δ: 0.70 (t, J=7.7 Hz, 3H), 0.93 (q, J=7.6 Hz, 2H), 3.56 (s, 6H), 6.87-6.97 (m, 3H), 7.29 (d, J=7.8 Hz, 2H); $^{13}$C NMR (DMSO-d$_6$, 100 MHz) δ: 8.21, 24.3, 35.7, 71.8, 124.1, 125.7, 132.3; $^{11}$B NMR (DMSO-d$_6$, 128 MHz) δ: 3.10

Compound (9): $^1$H-NMR (DMSO-d$_6$, 400 MHz) δ: 0.69 (t, J=7.6 Hz, 3H), 0.93 (q, J=7.6 Hz, 2H), 3.57 (s, 6H), 6.87-6.97 (m, 3H), 7.30 (d, J=7.8 Hz, 2H); $^{13}$C-NMR (DMSO-d$_6$, 100 MHz) δ: 8.20, 24.2, 36.7, 71.8, 124.2, 125.7, 132.3; $^{11}$B NMR (DMSO-d$_6$, 128 MHz) δ: 4.58

Compound (10): $^1$H NMR (DMSO-d$_6$, 400 MHz) δ: 0.69 (t, J=7.6 Hz, 3H), 0.93 (q, J=7.6 Hz, 2H), 3.57 (s, 6H), 6.87-6.98 (m, 3H), 7.29 (d, J=6.8 Hz, 2H); $^{13}$C NMR (DMSO-d$_6$, 100 MHz) δ: 8.21, 24.3, 36.7, 71.8, 124.1, 125.7, 132.3; $^{11}$B NMR (DMSO-d$_6$, 128 MHz) δ: 3.29

Compound (11): $^1$H NMR (DMSO-d$_6$, 400 MHz) δ: 0.70 (t, J=7.6 Hz, 3H), 0.93 (q, J=7.6 Hz, 2H), 3.57 (s, 6H), 6.87-6.98 (m, 3H), 7.30 (d, J=6.8 Hz, 2H); $^{13}$C NMR (DMSO-d$_6$, 100 MHz) δ: 8.21, 24.3, 36.7, 71.8, 124.2, 125.8, 132.4; $^{11}$B-NMR (DMSO-d$_6$, 128 MHz) δ: 3.43

Compound (12): $^1$H-NMR (DMSO-d$_6$, 400 MHz) δ: 0.69 (t, J=7.6 Hz, 3H), 0.92 (m, 14H), 1.29 (m, 8H), 1.54 (m, 8H), 3.14 (m, 8h), 3.56 (s, 6H), 6.86-6.96 (m, 3H), 7.29 (d, J=7.8 Hz, 2H); $^{13}$C-NMR (DMSO-d$_6$, 100 MHz) δ: 8.19, 13.7, 19.4, 23.2, 24.3, 33.9, 57.7, 71.8, 124.1, 125.6, 132.4; $^{11}$B-NMR (DMSO-d$_6$, 128 MHz) δ: 3.49

Compound (13): $^1$H NMR (270 MHz, DMSO-$d_6$) (s, 3H), 2.16 (s, 3H), 3.55 (s, 6H), 6.79 (d, J=7.3 Hz, 2H), 7.18 (d, J=7.8 Hz, 2H); $^{13}$C NMR (67.5 MHz, DMSO-$d_6$) δ: 16.5, 21.2, 34.6, 73.8, 126.5, 132.2, 132.3; MS m/z (%): 219 (M$^+$, 15), 218 (5), 191 (5), 149 (7), 148 (100), 147 (5), 146 (19); HRMS m/z: calcd. for $C_{12}H_{16}BO_3$ 219.1198, found 219.1197.

Compound (14): $^1$H NMR (400 MHz, DMSO-$d_6$) δ: 0.70 (s, 3H), 0.95 (q, J=5.3 Hz, 2H), 2.17 (s, 3H), 3.58 (s, 6H), 6.80 (d, J=4.9 Hz, 2H), 7.21 (d, J=4.9 Hz, 2H); $^{13}$C NMR (100 MHz, DMSO-$d_6$) δ: 8.17, 21.3, 24.2, 36.7, 71.5, 126.7, 132.4, 132.5; MS m/z (%): 233 (M$^+$, 100), 232 (26), 195 (36); HRMS m/z: calcd. for $C_{14}H_{14}O_2$ 233.1349, found 233.1341.

Compound (15): $^1$H NMR (270 MHz, DMSO-$d_6$) δ: 0.48 (s, 3H), 1.22 (s, 9H), 3.57 (s, 3H), 7.02 (d, J=7.4 Hz, 2H), 7.24 (d, J=7.5 Hz, 2H); $^{13}$C NMR (67.5 MHz, DMSO-$d_6$) δ: 16.5, 31.7, 34.0, 34.6, 73.6, 122.5, 132.1, 146.2; MS m/z (%): 261 (M$^+$, 19), 260 (5), 246 (4), 233 (15), 232 (5), 168 (9), 153 (15), 148 (100), 146 (21); HRMS m/z: calcd. for $C_{15}H_{22}BO_3$ 261.1668, found 261.1666.

Compound (16): $^1$H NMR (270 MHz, DMSO-$d_6$) δ: 0.48 (s, 3H), 3.57 (s, 6H), 3.64 (s, 3H), 6.57 (d, J=8.2 Hz, 2H), 7.22 (d, J=8.1 Hz, 2H); $^{13}$C NMR (67.5 MHz, DMSO-$d_6$) δ: 16.5, 34.6, 54.6, 73.8, 111.6, 133.1, 156.9.

Compound (17): $^1$H NMR (270 MHz, DMSO-$d_6$) δ: 0.49 (s, 3H), 3.61 (s, 6H), 6.69 (d, J=7.8 Hz, 2H), 6.89 (d, J=7.9 Hz, 2H), 7.02 (t, J=7.3 Hz, 1H), 7.37 (m, 4H); $^{13}$C NMR (67.5 MHz, DMSO-$d_6$) δ: 16.4, 34.6, 73.9, 117.2, 117.6, 122.3, 129.9, 133.7, 153.4, 158.5; MS m/z (%): 297 M$^+$, 1), 287 (1), 276 (2), 275 (14), 269 (20), 183 (95), 181 (18)

Compound (18): $^1$H NMR (270 MHz, DMSO-$d_6$) δ: 0.47 (s, 3H), 3.56 (s, 6H), 5.77 (s, 2H), 6.55 (s, 1H), 6.80 (s, 3H); $^{13}$C NMR (67.5 MHz, DMSO-$d_6$) δ: 16.4, 34.6, 73.8, 99.1, 106.7, 112.3, 124.8, 144.3, 145.5; MS m/z (%): 249 (M$^+$, 6), 248 (2), 192 (4), 148 (100), 146 (18), 195 (15), 183 (22), 170 (18); HRMS m/z: calcd. for $C_{12}H_{14}BO_5$ 249.0940, found 249.0927

Compound (19): $^1$H NMR (400 MHz, DMSO-$d_6$) δ: 0.66 (s, 3H), 3.82 (s, 6H), 7.33-7.69 (m, 6H), 8.96 (s, 1H); $^{13}$C NMR (100 MHz, DMSO-$d_6$) δ: 16.6, 34.9, 73.9, 122.9, 124.0, 125.0, 127.2, 129.3, 132.6, 133.4, 137.7

Compound (20): $^1$H NMR (270 MHz, DMSO-$d_6$) δ: 0.47 (s, 3H), 3.56 (s, 6H), 6.70-6.78 (m, 2H), 7.30 (d, J=7.5 Hz, 2H); $^{13}$C NMR (67.5 MHz, DMSO-$d_6$) δ: 16.5, 34.6, 73.8, 124.4, 126.0, 132.3; MS m/z (%): 223 (M$^+$, 13), 222 (3), 153 (12), 148 (100), 147 (6), 146 (22); HRMS m/z: calcd. for $C_{11}H_{14}BFO_3$ 223.0934, found 223.0947

Compound (21): $^1$H NMR (270 MHz, DMSO-$d_6$) δ: 0.49 (s, 3H), 3.60 (s, 6H), 7.30 (d, J=7.9 Hz, 2H), 7.52 (d, J=7.8 Hz, 2H); $^{13}$C NMR (67.5 MHz, DMSO-$d_6$) δ: 16.3, 34.7, 73.8, 122.13, 122.2, 122.2, 123.3, 123.6, 124.5, 124.9, 125.4, 127.6, 132.7; MS m/z (%): 273 (M$^+$, 25), 272 (6), 258 (6), 245 (15), 153 (10), 148 (100), 146 (24); HRMS m/z: calcd. for $C_{12}H_{13}BF_3O_3$ 273.0915, found 273.0919

Compound (22): $^1$H NMR (270 MHz, DMSO-$d_6$) δ: 0.49 (s, 3H), 3.61 (s, 6H), 7.20-7.27 (m, 2H), 7.59-7.65 (m, 2H); $^{13}$C NMR (67.5 MHz, DMSO-$d_s$) δ: 16.3, 34.8, 73.8, 121.2, 123.9, 126.7, 128.8, 136.2; HRMS m/z: calcd. for $C_{17}H_{19}BO_4$ 273.0915, found 273.0919

Compound (23): $^1$H NMR (270 MHz, DMSO-$d_6$) δ: 0.48 (s, 3H), 2.50 (s, 3H), 3.58 (s, 6H), 7.44-7.72 (m, 4H)

Compound (24): $^1$H NMR (270 MHz, DMSO-$d_5$) δ: 0.50 (S, 3H), 3.59 (s, 6H), 6.98 (s, 1H), 7.60 (s, 1H), 8.15 (s, 1H), 8.43 (s, 1H); $^{13}$C NMR (67.5 MHz, DMSO-$d_6$) δ: 16.4, 34.7, 73.7, 122.1, 139.5, 145.7, 153.6; MS m/z (%): 206 (M$^+$, 8), 205 (2), 192 (4), 186 (3), 178 (4), 175 (7), 153 (7), 149 (7), 148 (100); HRMS m/z: calcd. for $C_{10}H_{13}BNO_3$ 298.1376, found 298.1375

Compound (26): $^1$H NMR (270 MHz, DMSO-$d_6$) δ: 0.54 (s, 3H), 2.35 (s, 3H), 3.67 (s, 6H), 6.91 (d, J=7.56 Hz, 1H), 7.12 (d, J=7.56 Hz, 1H), 7.40 (t, J=7.56 Hz, 1H)

Compound (27): $^1$H NMR (270 MHz, DMSO-$d_6$) δ: 0.46 (s, 3H), 3.54 (s, 6H), 6.81-7.08 (m, 3H); $^{13}$C NMR (67.5 MHz, DMSO-$d_6$) δ: 16.3, 73.8, 123.5, 126.1, 126.6

Compound (28): $^1$H NMR (270 MHz, DMSO-$d_6$) δ: 0.49 (s, 3H), 3.59 (s, 6H), 7.36-8.02 (m, 5H)

Compound (29): $^1$H NMR (270 MHz, DMSO-$d_6$) δ: 0.45 (s, 3H), 3.54 (s, 6H), 6.84-7.03 (m, 3H)

Compound (30): $^1$H NMR (400 MHz, DMSO-$d_6$) δ: 0.64 (t, J=7.6 Hz, 3H), 0.82-0.88 (m, 5H), 1.22 (m, 4H), 1.79-1.84 (m, 2H), 3.44 (s, 6H), 5.09 (d, J=18.0 Hz, 1H), 5.33 (dt, J=18.0, 6.3 Hz, 1H); $^{13}$C NMR (100 MHz, DMSO-$d_6$) δ: 8.13, 14.2, 22.1, 24.2, 31.9, 35.6, 36.5, 71.4, 133.0; $^{11}$B NMR (128 MHz, DMSO-$d_6$) δ: 0.37

Compound (31): $^1$H NMR (270 MHz, DMSO-$d_6$) δ: 0.45 (s, $^3$H), 3.55 (s, 6H), 5.14 (br s, 2H), 7.11-7.53 (m, 5H); $^{13}$C NMR (67.5 MHz, DMSO-$d_6$) δ: 16.4, 34.6, 73.6, 116.5, 124.4, 126.8, 127.6, 147.8

Compound (32): $^1$H NMR (270 MHz, DMSO-$d_6$) δ: −0.23 (m, 2H), 0.37 (s, 3H), 0.76 (t, J=6.8, 3H), 1.05-1.12 (m, 4H), 3.39 (s, 6H); $^{13}$C NMR (67.5 MHz, DMSO-$d_6$) δ: 14.7, 16.6, 26.7, 28.8, 34.2, 73.5

Compound (33): $^1$H NMR (270 MHz, DMSO-$d_6$) δ: −0.25 (m, 2H), 0.37 (s, 3H), 0.84 (t, J=6.6 Hz, 3H), 1.05-1.19 (m, 12H), 3.38 (s, 6H); $^{13}$C NMR (67.5 MHz, DMSO-$d_6$) δ: 14.2, 16.6, 22.4, 26.3, 29.2, 29.7, 31.7, 34.1, 34.2, 73.5

Compound (34): $^1$H NMR (270 MHz, CDCl$_3$/DMSO-$d_6$) δ: 0.85 (br s, 6H), 1.05-1.57 (m, 8H), 2.09 (br s, 2H), 3.51 (br.s, 6H)

Example 37

Cross coupling reaction by palladium catalyst: under nitrogen atmosphere, palladium acetate (3 mol %), 2-bromoanisol (1.0 mmol) and p-tolyltriol borate potassium salt (compound (13), 1.1 mmol) were dissolved in the solution of DMF/H$_2$O (3 ml) (DMF/H$_2$O=5/1), and the reaction solution was stirred at 25° C. for 22 hours. After extraction, it was purified by column chromatography to obtain the product (formula (X), yield: 98%).

[Physical Property Data]

$^1$H-NMR (CDCl$_3$, 400 MHz) δ: 2.37 (s, 3H), 3.76 (s, 3H), 6.93-7.02 (m, 1H), 7.19-7.31 (m, 5H), 7.39-7.44 (m, 2H); $^{13}$C-NMR (CDCl$_3$, 100 MHz) δ: 21.1, 55.4, 111.1, 120.7, 128.3, 128.6, 129.3, 130.7, 135.5, 136.5, 156.4; MS (m/z) 115(6), 128(6), 139(5), 155(16), 167(15), 198(100, M$^+$); exact mass calcd for $C_{14}H_{14}O$: 198.1049; found 198.1045.

[Formula 13]

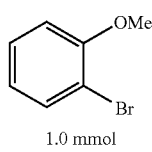

(X)

1.0 mmol    +

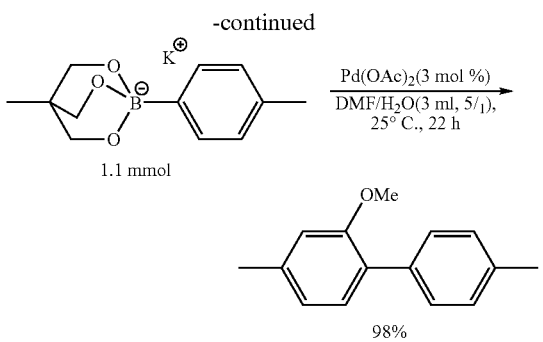

Example 38

1,4-addition reaction by Rhodium catalyst: under nitrogen atmosphere, in the presence of [Rh(nbd)((R)-binap)]BF₄ (3 mol %), 2-cyclohexenone (1 mmol), p-tolyltriol borate potassium salt (compound (13), 1.5 mmol) were dissolved in the solution of DME/H₂O (1.9 ml, 18/1), and the reaction solution was stirred at 80° C. for 16 hours. After extraction, it was purified by column chromatography to obtain the product (formula (XI), yield: 88%, optical isomeric excess: 97% ee). (nbd: 2,5-norbornadiene, (R)-binap: (R)-2,2'-bis(diphenylphosphino)-1,1'-binaphthyl)

[Physical Property Data]

$^1$H-NMR (CDCl$_3$, 400 MHz) δ: 1.70-1.88 (m, 2H), 2.01-2.19 (m, 2H), 2.33 (s, 3H), 2.36-2.60 (m, 4H), 2.97 (tt, J=11.6 and 4.0 Hz, 1H), 7.10-7.15 (m, 4H); $^{13}$C-NMR (CDCl$_3$, 100 MHz) δ: 20.9, 25.5, 32.8, 41.1, 44.3, 49.0, 126.4, 129.3, 136.2, 141.4, 211.2; MS (m/z) 77(9), 83(10), 94(38), 105 (19), 118 (39), 131(100), 145(26), 173(5), 188(57, M⁺); exact mass calcd for C$_{13}$H$_{16}$O: 188.1201; found 188.1201.

[Formula 14]

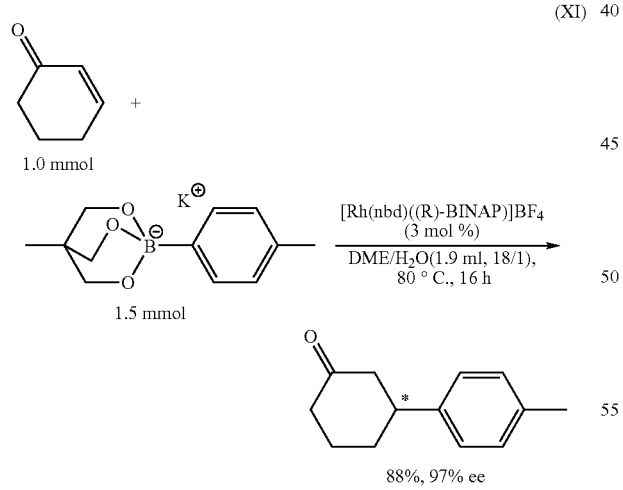

Example 39

1,2-addition reaction By rhodium catalyst: under nitrogen atmosphere, [Rh(coe)₂Cl]₂ (1.5 mol %) and diphenylphosphinopropane (dppp, 3 mol %) were dissolved in the solution of DME/H₂O (3 ml, 1/1), and then, 1-naphthaldehyde (1.0 mmol) and p-tolyltriol borate potassium salt (compound (13), 1.5 mmol) were added to the reaction solution, it was stirred at 25° C. for 16 hours. After extraction, it was purified by column chromatography to obtain the product (formula (XII), yield: 89%). (coe: cis-cyclooctene)

[Physical Property Data]

$^1$H-NMR (CDCl$_3$, 400 MHz) δ: 2.3 (s, 3H), 2.46 (bs, 1H), 6.41 (bs, 1H), 7.08 (d, J=8.3 Hz, 2H), 7.23 (d, J=8.3 Hz, 2H), 7.35-7.46 (m, 3H), 7.60 (d, J=7.3 Hz, 1H), 7.72-7.83 (m, 2H), 7.95 (d, J=7.8 Hz, 1H); $^{13}$C-NMR (CDCl$_3$, 100 MHz) δ: 21.1, 73.3, 123.9, 124.3, 125.3, 125.5, 126.0, 127.0, 128.3, 128.7, 129.1, 130.6, 133.8, 137.3, 138.8, 140.2.

[Formula 15]

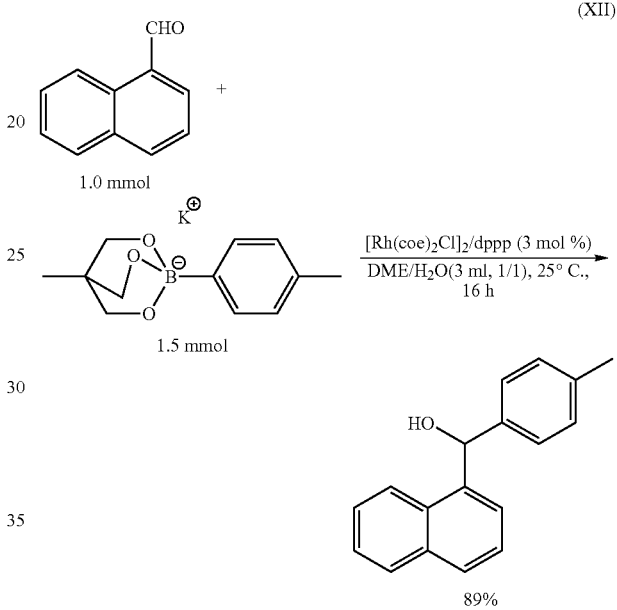

Example 40

Amination reaction by copper catalyst: under oxygen atmosphere, into the solution of copper acetate (10 mol %), p-tolyltriol borate potassium salt (formula (V), 1.5 mmol), molecular sieve 4A (300 mg) in toluene (6 ml), piperidine (1.0 mmol) was added, and the reaction solution was stirred at 25° C. for 20 hours. Reaction mixture was filtrated through celite, and after condensing the filtrate, it was purified by column chromatography to obtain the product (formula (XIII), yield: 95%).

[Physical Property Data]

$^1$H-NMR (CDCl$_3$, 400 MHz) δ: 1.55-1.71 (m, 6H), 2.26 (s, 3H), 3.09 (t, J=5.12 Hz, 4H), 6.86 (d, J=8.5 Hz, 2H), 7.06 (d, J=8.5 Hz, 2H); $^{13}$C-NMR (CDCl$_3$, 100 MHz) δ: 20.4, 24.3, 25.9, 51.3, 116.9, 128.7, 129.5, 150.3.

[Formula 16]

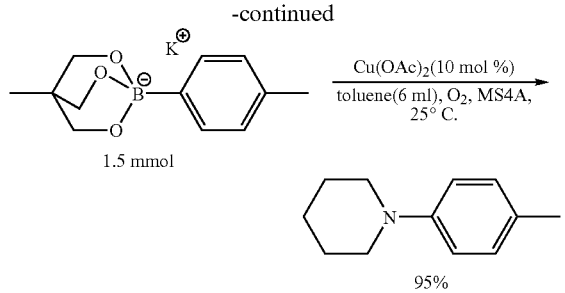

Examples 41 to 45

Cross coupling reaction by palladium catalyst of 2-pyridine borate lithium salt (compound (26)): under nitrogen atmosphere, palladium acetate, ligand, copper iodide, halogenated compound (1.0 mmol) and 2-pyridine triol borate lithium salt (compound (26), 1.1 mmol) were dissolved in DMF (3 ml), and the reaction solution was stirred at 80 to 100° C. for 22 hours. After extraction, it was purified by column chromatography to obtain the product. Results were shown in Table-2.

[Formula 17]

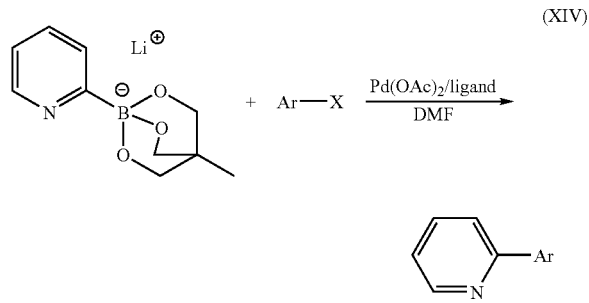

It should be noted that, physical data obtained from examples 41 to 45 are as follows:

Example 41; 2-(4-nitrophenyl)pyridine: $^1$H-NMR (CDCl$_3$, 270 MHz) δ: 7.07 (br s, 1H), 7.54 (br s, 2H), 7.89 (d, J=7.1 Hz, 2H), 8.03 (d, J=7.1 Hz, 2H), 8.47 (br s, 1H); $^{13}$C-NMR (CDCl$_3$, 67.5 MHz) a: 121.1, 123.4, 123.9, 127.5, 137.0, 145.1, 148.0, 145.0, 154.6

Example 42; 1-(4-(pyridin-2-yl)phenyl)ethanone: $^1$H-NMR (CDCl$_3$, 270 MHz) δ: 7.39 (dd, J=4.8, 7.9 Hz, 1H), 7.67 (d, J=8.4 Hz, 2H), 7.90 (dt, J=2.0, 7.9 Hz, 1H), 8.06 (d, J=8.4 Hz, 2H), 8.64 (dd, J=1.5, 4.8 Hz, 1H), 8.87 (d, J=2.0 Hz, 1H); $^{13}$C-NMR (CDCl$_3$, 67.5 MHz) δ: 26.4, 123.4, 126.9, 128.8, 134.2, 135.0, 136.2, 142.0, 148.0, 149.0, 197.2

Example 43

2,2'-bipyridine: $^1$H-NMR (CDCl$_3$, 270 MHz) δ: 7.25-7.33 (m, 2H), 7.73-7.85 (m, 2H), 8.40 (d, J=7.9 Hz, 2H), 8.69 (d, J=4.5 Hz, 1H); $^{13}$C-NMR (CDCl$_3$, 67.5 MHz) δ: 121.1, 123.7, 136.9, 149.1, 156.0

Example 44; 2-(4-methoxyphenyl)pyridine: $^1$H-NMR (CDCl$_3$, 270 MHz) δ: 3.77 (s, 3H), 6.91 (d, J=8.9 Hz, 2H), 7.05-7.10 (m, 1H), 7.56-7.65 (m, 2H), 7.87 (dt, J=2.4, 6.7 Hz, 2H), 8.56 (d, J=4.7 Hz, 1H); $^{13}$C-NMR (CDCl$_3$, 67.5 MHz) δ: 55.3, 114.1, 119.8, 121.3, 128.1, 132.0, 136.6, 149.5, 157.0, 160.4

Example 45; 2-p-tolylpyridine: $^1$H-NMR (CDCl$_3$, 270 MHz) δ: 2.40 (s, 3H), 7.16-7.21 (m, 1H), 7.27 (d, J=8.0 Hz, 2H), 7.70-7.71 (m, 2H), 7.89 (d, J=8.0 Hz, 2H), 8.67 (d, J=4.7 Hz, 1H); $^{13}$C-NMR (CDCl$_3$, 67.5 MHz) δ: 21.2, 120.2, 121.7, 126.7, 129.4, 136.6, 138.9, 149.5, 157.4

When organic synthesis reaction was carried out by using organic triol borate salts of the present invention, the said organic triol borate salts of the present invention can be used as the stable and high reactive nucleophilic agent without such problems having in the conventional reagents of organic boronic acid that, for example, the product as pure compound cannot be isolated because of trimerization with dehydration;

TABLE 2

| | Ar-X | Condition | Product | Yield (%) |
|---|---|---|---|---|
| Example 41 | O$_2$N—⟨phenyl⟩—Br | Pd(OAc)$_2$(3 mol %)/PPh$_3$(6·6 mol %) CuI(20 mol %) 80° C., 22h | ⟨pyridyl⟩—⟨phenyl⟩—NO$_2$ | 90 |
| Example 42 | Ac—⟨phenyl⟩—Br | Pd(OAc)$_2$(3 mol %)/PPh$_3$(6·6 mol %) CuI(20 mol %) 80° C., 22 h | ⟨pyridyl⟩—⟨phenyl⟩—Ac | 75 |
| Example 43 | ⟨pyridyl⟩—Br | Pd(OAc)$_2$(3 mol %)/PPh$_3$(6·6 mol %) CuI(40 mol %) 80° C., 22 h | ⟨pyridyl⟩—⟨pyridyl⟩ | 70 |
| Example 44 | MeO—⟨phenyl⟩—I | Pd(OAc)$_2$(6 mol %)/XantPhos(6·6 mol %) CuI(40 mol %) 100° C., 22 h | ⟨pyridyl⟩—⟨phenyl⟩—OMe | 74 |
| Example 45 | Me—⟨phenyl⟩—I | Pd(OAc)$_2$(6 mol %)/XantPhos(6·6 mol %) CuI(40 mol %) 100° C., 22 h | ⟨pyridyl⟩—⟨phenyl⟩—Me | 77 | the reagents are needed to activate by base due to lower chemical activity; the reagent is easily hydrolized due to the reaction in such a basic aqueous solution; for example, the reagent having the structure such as pyridine boronic acid, thiophene boronic acid, pyrrole boronic acid, furan boronic acid, or alkynylboronic acid has not been used as the reagent for the organic synthesis reaction.

In addition, the organic trial borate salts of the present invention obtained from example 18 [compound (16)] and example 25 [compound (23)] have been found not to decompose in THF/water mixed solvent even after 130 hours elapsed. Namely, the organic triol borate salts of the present invention were found to be excellent in the stability of storage.

Example 46

The solution of 1,4-phenylene bisboronic acid (60 mmol) and 1,1,1-tris(hydroxymethyl)ethane (132 mmol) in toluene (120 ml) was heated under reflux for 3 hours, extracted by ethyl acetate, and then, into the toluene solution of the solid obtained by removing the solvent, potassium hydroxide (120 mmol) was added, further, the solution was heated under reflux for 4 hours. After completing the reaction, this was cooled to room temperature, filtrated, and the resulting solid was dried under reduced pressure. Product yield was 99%, the product was identified as 1,4-phenylene bis triol borate potassium salt (compound (36), formula (XX)).

[Formula 23]

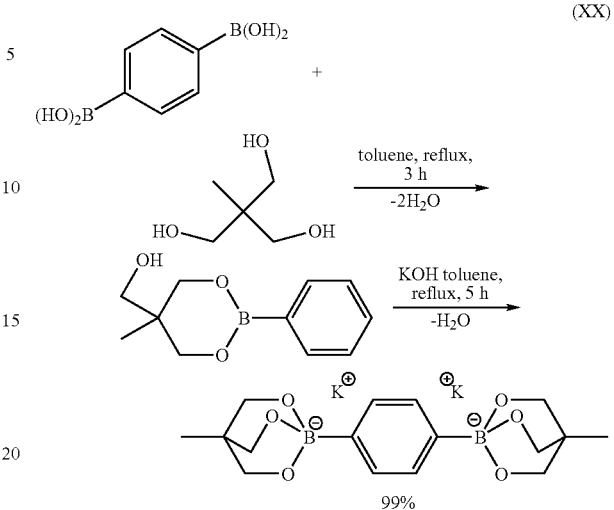

Examples 47 to 51

The objects were obtained by carrying out in a similar manner to example 46 except using the boronic acid described in Table-3 instead of 1,4-phenylene bisboronic acid of example 46, the results thereof were shown additionally.

TABLE 3

| | Boronic acid | Compound | | Yield |
|---|---|---|---|---|
| Example 47 |  | (37) | 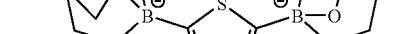 | 67% |
| Example 48 | 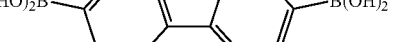 | (38) | 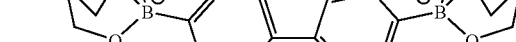 | 45% |
| Example 49 | 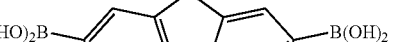 | (39) | 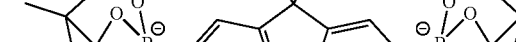 | 68% |
| Example 50 |  | (40) | 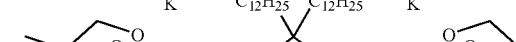 | 83% |

TABLE 3-continued

| | Boronic acid | Compound | Yield |
|---|---|---|---|
| Example 51 | 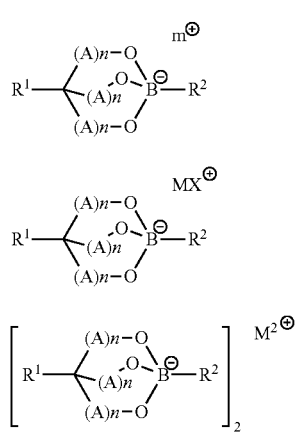 | 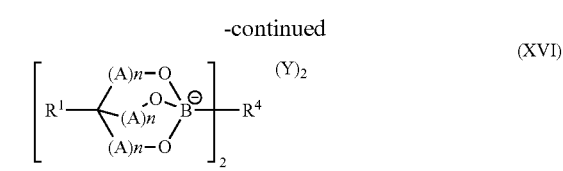 | 87% |

It should be noted that, physical property data of the organic triol borate salts of the present invention obtained from examples 46 to 51 are as follows:

Compound (36); $^1$H NMR (400 MHz, DMSO-$d_6$) δ: 0.43 (s, 6H), 3.52 (5, 12H), 6.95 (s, 4H)

Compound (37): $^1$H NMR (400 MHz, DMSO-$d_6$) δ: 0.42 (s, 6H), 3.51 (s, 12H), 6.48 (s, 2H); $^{13}$C NMR (100 MHz, DMSO-$d_6$) δ: 16.7, 39.8, 74.1, 127.3

Compound (38); $^1$H NMR (400 MHz, DMSO-$d_6$) δ: 0.49 (s, 6H), 0.71 (br s, 6H), 0.71-0.74 (m, 4H), 1.00-1.07 (m, 12H), 1.80 (br s, 4H), 3.58 (s, 12H), 7.18-7.24 (m, 6H)

Compound (39); $^1$H NMR (400 MHz, DMSO-$d_6$) δ: 0.43 (5, 6H), 0.53 (br s, 6H), 0.76-0.79 (m, 4H), 0.97-1.14 (m, 20H), 1.80 (br s, 4H), 3.59 (s, 12H), 7.25-7.45 (m, 6H)

Compound (40); $^1$H NMR (400 MHz, DMSO-$d_6$) δ: 0.43 (s, 6H), 0.56 (br s, 6H), 0.81-0.85 (m, 4H), 0.97-1.18 (m, 36H), 1.83 (br s, 4H), 3.60 (5, 12H), 7.26-7.31 (m, 6H)

Compound (41); $^1$H NMR (400 MHz, DMSO-$d_6$) δ: 0.42 0.86 (m, 34H), 1.84 (br s, 4H), 3.60 (s, 12H), 7.31-7.42 (m, 6H)

When the organic triol borate salts represented by general formula (XVI) of the present invention were used, for example, carbon-carbon formation reaction by cross coupling reaction can be effectively carried out.

The invention claimed is:

1. A reagent for organic synthesis reaction comprising at least one among organic triol borate salts represented by the following general formulae (I) to (III) and (XVI):

 (I)

 (II)

$$\left[ \begin{matrix} (A)n-O \\ R^1 \underset{(A)n}{\overset{O}{\diagdown}} \overset{O}{\underset{(A)n-O}{\diagdown}} B^\ominus - R^2 \end{matrix} \right]_2 M^{2\oplus}$$ (III)

$$\left[ R^1 \underset{(A)n}{\overset{(A)n-O}{\diagdown}} \overset{O}{\underset{(A)n-O}{\diagdown}} B^\ominus - R^4 \right]_2 (Y)_2$$ (XVI)

wherein, $R^1$ represents alkyl group, alkenyl group, alkynyl group, aryl group or aralkyl group; $R^2$ represents alkyl group, alkenyl group, alkynyl group, aryl group, aralkyl group or heterocyclic group, which may have a substituent group, or hydrogen atom; $R^4$ represents a divalent aromatic hydrocarbon group or heterocyclic group, which may have a substituent group; $m^+$ represents alkaline metal ion, phosphonium ion, or ammonium ion represented by general formula (IV):

$$\overset{\oplus}{N(R^3)_4}$$ (IV)

wherein, $R^3$ represents an alkyl group); $M^{2+}$ represents an alkaline earth metal ion, X represents halogen or alkoxide; Y represents alkaline metal ion, phosphonium ion, ammonium ion represented by general formula (IV), or the group represented by general formula (XVII):

$$MX^\oplus$$ (XVII)

wherein, M represents an alkaline earth metal, X represents halogen atom or alkoxide; A represents a methylene group which may have a substituent group; each n represents an integer of 1 to 10 and may be the same or the different, respectively.

2. The reagent for organic synthesis reaction according to claim 1, wherein n is 1 and A is a methylene group.

3. The reagent for organic synthesis reaction according to claim 1, wherein $R^1$ is methyl group, ethyl group or tert-butyl group.

4. The reagent for organic synthesis reaction according to claim 1, wherein $R^4$ is the group represented by general formula (XVIII):

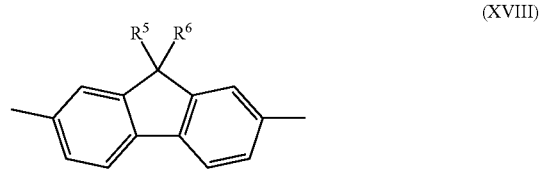 (XVIII)

(wherein, $R^5$ and $R^6$ represent each independently alkyl group), phenylene group or the group represented by the following formula (XIX):

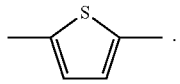

(XIX)

5. The reagent for organic synthesis reaction according to claim 1, wherein the organic synthesis reaction using the aforesaid reagent for organic synthesis reaction is carbon-carbon bond formation reaction, carbon-nitrogen bond formation reaction, carbon-oxygen bond formation reaction or carbon-sulfur bond formation reaction.

6. The reagent for organic synthesis reaction according to claim 1, wherein the organic synthesis reaction using the aforesaid reagent for organic synthesis reaction is cross coupling reaction or addition reaction.

7. A cross coupling reaction method, which comprises reacting the reagent for organic synthesis reaction according to claim 1 with organic halogenated compound, amine, alcohol or thioalcohol compound in the presence of palladium catalyst, nickel catalyst or copper catalyst.

8. An addition reaction method, which comprises reacting the reagent according to claim 1 for organic synthesis reaction with the electron-withdrawing group substituted olefin compound, carbonyl compound or imine compound in the presence of rhodium catalyst or palladium catalyst.

9. An organic borate salt represented by the following general formulae (I) to (III) and (XVI):

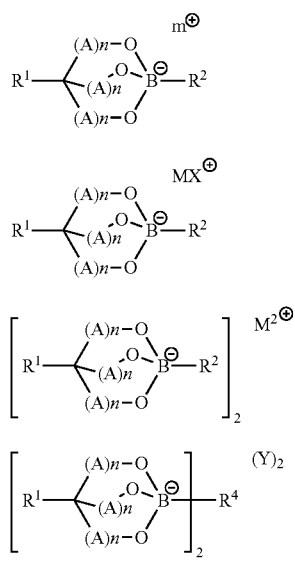

wherein, $R^1$ represents alkyl group, alkenyl group, alkynyl group, aryl group or aralkyl group; $R^2$ represents alkyl group, alkenyl group, alkynyl group, aryl group, aralkyl group or heterocyclic group, which may have a substituent group or hydrogen atom; $R^4$ represents divalent aromatic hydrocarbon group or heterocyclic group, which may have a substituent group; $m^+$ represents alkaline metal ion, phosphonium ion or ammonium ion represented by general formula (IV):

wherein, $R^3$ represents an alkyl group); $M^{2+}$ represents an alkaline earth metal ion, X represents halogen or alkoxide; Y represents alkaline metal ion, phosphonium ion, ammonium ion represented by general formula (IV), or the group represented by general formula (XVII):

$$MX^\oplus \qquad (XVII)$$

wherein, M represents an alkaline earth metal, X represents halogen atom or alkoxide; A represents a methylene group which may have a substituent group; each n represents an integer of 1 to 10 and may be the same or the different, respectively.

10. The organic triol borate salt according to claim 9, wherein n is 1, and A is a methylene group.

11. The organic triol borate salt according to claim 9, wherein $R^1$ is methyl group, ethyl group or tert-butyl group.

12. The organic triol borate salt according to claim 9, wherein $R^2$ is a heterocyclic group selected from the groups consisting of thienyl group, pyridyl group, thiophenyl group, furanyl group and pyrrolyl group, or alkynyl group.

13. The organic triol borate salt according to claim 9, wherein $R^4$ is the group represented by general formula (XVIII):

(XVIII)

(wherein, $R^5$ and $R^6$ represent each independently alkyl group), phenylene group or the group represented by the following formula (XIX):

[Formula 21]

(XIX)

\* \* \* \* \*